United States Patent
Borzilleri et al.

(10) Patent No.: US 7,566,784 B2
(45) Date of Patent: Jul. 28, 2009

(54) BICYCLIC HETEROCYCLES AS KINASE INHIBITORS

(75) Inventors: Robert M. Borzilleri, New Hope, PA (US); Kyoung S. Kim, North Brunswick, NJ (US); Zhen-Wei Cai, Belle Mead, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 613 days.

(21) Appl. No.: 11/113,838

(22) Filed: Apr. 25, 2005

(65) Prior Publication Data

US 2005/0239820 A1 Oct. 27, 2005

Related U.S. Application Data

(60) Provisional application No. 60/565,381, filed on Apr. 26, 2004.

(51) Int. Cl.
C07D 487/04 (2006.01)
(52) U.S. Cl. .................................................. 546/113
(58) Field of Classification Search ................ 546/113
See application file for complete search history.

(56) References Cited

U.S. PATENT DOCUMENTS

| | | | |
|---|---|---|---|
| 3,646,202 A | 2/1972 | Mrozik | |
| 4,602,912 A | 7/1986 | de Sousa et al. | |
| 4,663,341 A | 5/1987 | Jacobson | |
| 4,753,940 A | 6/1988 | Sturm et al. | |
| 4,845,093 A | 7/1989 | Haga et al. | |
| 4,908,056 A | 3/1990 | Tseng | |
| 5,132,314 A | 7/1992 | Maienfisch et al. | |
| 5,135,949 A | 8/1992 | von der Saal et al. | |
| 5,646,176 A | 7/1997 | Golik et al. | |
| 6,022,884 A | 2/2000 | Mantlo et al. | |
| 6,143,743 A | 11/2000 | Wilde et al. | |
| 6,143,764 A | 11/2000 | Kubo et al. | |
| 6,214,344 B1 | 4/2001 | Schwall et al. | |
| 6,232,320 B1 | 5/2001 | Stewart et al. | |
| 6,262,094 B1 | 7/2001 | Hoefle et al. | |
| 6,353,007 B1 | 3/2002 | Sharma | |
| 6,355,660 B1 | 3/2002 | Ricks et al. | |
| 6,380,386 B2 | 4/2002 | Seitz et al. | |
| 6,429,213 B1 | 8/2002 | Xue et al. | |
| 6,521,622 B1 | 2/2003 | Ricks et al. | |
| 6,559,341 B2 | 5/2003 | Tohnishi et al. | |
| 6,603,044 B1 | 8/2003 | Tohnishi et al. | |
| 6,620,827 B2 | 9/2003 | De la Brouse-Elwood et al. | |
| 6,696,487 B2 | 2/2004 | Gerusz et al. | |
| 6,706,740 B2 | 3/2004 | Ricks et al. | |
| 6,750,246 B1 | 6/2004 | Kadow et al. | |
| 6,825,184 B2 | 11/2004 | Cirillo et al. | |
| 6,858,626 B2 | 2/2005 | Xue et al. | |
| 6,869,952 B2 | 3/2005 | Bhide et al. | |
| 6,900,208 B2 | 5/2005 | Salvati et al. | |
| 6,982,265 B1 | 1/2006 | Hunt et al. | |
| 7,030,112 B2 | 4/2006 | Salvati et al. | |
| 2001/0041673 A1 | 11/2001 | Fossa | |
| 2003/0082631 A1 | 5/2003 | Gustavsson et al. | |
| 2003/0162968 A1 | 8/2003 | Cirillo et al. | |
| 2003/0232765 A1 | 12/2003 | Carter et al. | |
| 2003/0232831 A1 | 12/2003 | Dyckman et al. | |
| 2004/0044203 A1 | 3/2004 | Wittman et al. | |
| 2004/0048891 A1 | 3/2004 | Kato et al. | |
| 2004/0053908 A1 | 3/2004 | Funahashi et al. | |
| 2004/0072832 A1 | 4/2004 | Bhide et al. | |
| 2004/0082582 A1 | 4/2004 | Dyckman et al. | |
| 2004/0209886 A1 | 10/2004 | Salvati et al. | |
| 2004/0229877 A1 | 11/2004 | Leftheris et al. | |
| 2004/0242603 A1 | 12/2004 | Fujiwara et al. | |
| 2005/0038035 A1 | 2/2005 | Takasugi et al. | |
| 2005/0043306 A1 | 2/2005 | Leftheris et al. | |
| 2005/0143398 A1 | 6/2005 | Das et al. | |
| 2005/0245530 A1 | 11/2005 | Borzilleri et al. | |
| 2005/0288289 A1 | 12/2005 | Crispino et al. | |
| 2005/0288290 A1 | 12/2005 | Borzilleri et al. | |
| 2006/0004006 A1 | 1/2006 | Borzilleri et al. | |

FOREIGN PATENT DOCUMENTS

| | | |
|---|---|---|
| AU | 200195986 | 4/2002 |
| DE | 31 39 457 | 4/1983 |
| DE | 197 10 609 | 9/1998 |
| EP | 0 151 962 | 8/1985 |

(Continued)

OTHER PUBLICATIONS

Kempter, G. et al., "Synthesis of potential plant protective agents and pesticides from substituted anilines", Wissenschaftliche Zeitschrift, vol. 27, No. 1, pp. 101-120 (1983) (with English abstract).
Search Report "A", dated Jul. 2, 2003.
Dumas, J. et al., "Synthesis and Structure Activity Relationships of Novel Small Molecule Cathepsin D Inhibitors", Bioorganic & Medicinal Chemistry Letters, vol. 9, pp. 2531-2536 (1999).
Kurogi, Y. et al., "Discovery of Novel Mesangial Cell Proliferation Inhibitors Using a Three-Dimensional Database Searching Method", J. Med. Chem., vol. 44, No. 14, pp. 2304-2307 (2001).

(Continued)

Primary Examiner—Patricia L Morris
(74) Attorney, Agent, or Firm—Gary D. Greenblatt; Maureen S. Gibbons

(57) ABSTRACT

The compounds of the instant invention can be used as anti-cancer agents. More specifically, the invention comprises a compound having Formula I or II,

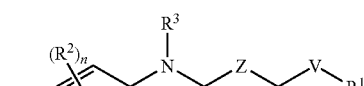

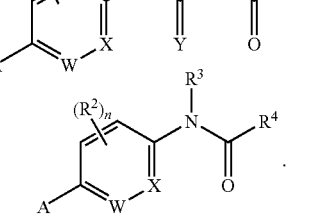

11 Claims, No Drawings

FOREIGN PATENT DOCUMENTS

| | | |
|---|---|---|
| EP | 0 119 774 | 6/1987 |
| EP | 0 152 910 | 7/1989 |
| EP | 0 919 542 | 6/1999 |
| EP | 1 243 582 | 9/2002 |
| EP | 1 411 046 | 4/2004 |
| GB | 2 106 500 | 4/1983 |
| JP | 54-115384 | 9/1979 |
| JP | 57-51835 | 3/1982 |
| JP | 62-62 | 1/1987 |
| JP | 62-5959 | 1/1987 |
| JP | 62-5960 | 1/1987 |
| JP | 62-135463 | 6/1987 |
| JP | 2003-321472 | 11/2003 |
| SU | 1761753 | 9/1992 |
| WO | WO 91/17162 | 11/1991 |
| WO | WO 97/17329 | 5/1997 |
| WO | WO 98/41513 | 9/1998 |
| WO | WO 99/01454 | 1/1999 |
| WO | WO 99/02514 | 1/1999 |
| WO | WO 99/24404 | 5/1999 |
| WO | WO 00/43366 | 7/2000 |
| WO | WO 00/50405 | 8/2000 |
| WO | WO 00/56738 | 9/2000 |
| WO | WO 00/71129 | 11/2000 |
| WO | WO 00/75145 | 12/2000 |
| WO | WO 01/21576 | 3/2001 |
| WO | WO 01/21596 | 3/2001 |
| WO | WO 01/42243 | 6/2001 |
| WO | WO 01/47890 | 7/2001 |
| WO | WO 01/94353 | 12/2001 |
| WO | WO 02/32872 | 4/2002 |
| WO | WO 02/40486 | 5/2002 |
| WO | WO 02/44156 | 6/2002 |
| WO | WO 02/051397 | 7/2002 |
| WO | WO 02/085859 | 10/2002 |
| WO | WO 03/000194 | 1/2003 |
| WO | WO 03/000660 | 1/2003 |
| WO | WO 03/011028 | 2/2003 |
| WO | WO 03/033472 | 4/2003 |
| WO | WO 03/042172 | 5/2003 |
| WO | WO 03/080610 | 10/2003 |
| WO | WO 03/082208 | 10/2003 |
| WO | WO 03/091229 | 11/2003 |
| WO | WO 03/099286 | 12/2003 |
| WO | WO 2004/001059 | 12/2003 |
| WO | WO 2004/002410 | 1/2004 |
| WO | WO 2004/032846 | 4/2004 |
| WO | WO 2004/048386 | 6/2004 |
| WO | WO 2004/054514 | 7/2004 |
| WO | WO 2004/058144 | 7/2004 |
| WO | WO 2004/060305 | 7/2004 |
| WO | WO 2005/005389 | 1/2005 |
| WO | WO 2005/010009 | 2/2005 |
| WO | WO 2005/021554 | 3/2005 |
| WO | WO 2005/026124 | 3/2005 |
| WO | WO 2005/030140 | 4/2005 |
| WO | WO 2005/042537 | 5/2005 |
| WO | WO 2005/058891 | 6/2005 |
| WO | WO 2005/082854 | 9/2005 |
| WO | WO 2005/082855 | 9/2005 |
| WO | WO 2005/097790 | 10/2005 |

OTHER PUBLICATIONS

U.S. Appl. No. 11/111,144, filed Apr. 21, 2005, Borzilleri et al.
U.S. Appl. No. 11/165,875, filed Jun. 24, 2005, Crispino et al.
U.S. Appl. No. 11/167,043, filed Jun. 24, 2005, Borzilleri et al.
U.S. Appl. No. 11/167,049, filed Jun. 24, 2005, Borzilleri et al.
Search Report "A", dated Dec. 16, 2004.

Hunt, J.T. et al., "Discovery of the Pyrrolo[2,1-*f*][1,2,4]triazine Nucleus as a New Kinase Inhibitor Template", J. Med. Chem., vol. 47, No. 16, pp. 4054-4059 (2004).

Okada, H. et al., "Synthesis and Antitumor Activities of Novel Benzoylphenylurea Derivatives", Chem. Pharm. Bull., vol. 39, No. 9, pp. 2308-2315 (1991).

Xue, C.-B. et al., "Rational Design, Synthesis and Structure-Activity Relationships of a Cyclic Succinate Series of TNF-α Converting Enzyme Inhibitors. Part 2: Lead Optimization", Bioorganic & Medicinal Chemistry Letters, vol. 13, pp. 4299-4304 (2003).

U.S. Appl. No. 09/573,829, filed May 18, 2000, Hunt et al.

Bardelli, A. et al., "Concomitant activation of pathways downstream of Grb2 and PI 3-kinase is required for *MET*-mediated metastasis", Oncogene, vol. 18, pp. 1139-1146 (1999).

Bottaro, D.P. et al., "Identification of the Hepatocyte Growth Factor Receptor as the c-*met* Proto-Oncogene Product", Science, vol. 251, pp. 802-804 (1991).

Bussolino, F. et al., "Hepatocyte Growth Factor Is a Potent Angiogenic Factor Which Stimulates Endothelial Cell Motility and Growth", The Journal of Cell Biology, vol. 119, No. 3, pp. 629-641 (1992).

Camp, R.L. et al., "*Met* Expression Is Associated with Poor Outcome in Patients with Axillary Lymph Node Negative Breast Carcinoma", Cancer, vol. 86, No. 11, pp. 2259-2265 (1999).

Cheng, C.-C. et al., "Comprehensive Studies on Dual Excitation Behavior of Double Proton versus Charge Transfer in 4-(*N*-Substituted amino)-1H-pyrrolo[2,3-*b*]pyridines", J. Phys. Chem. A, vol. 107, No. 10, pp. 1459-1471 (2003).

Christensen, J.G. et al., "A Selective Small Molecule Inhibitor of c-Met Kinase Inhibits c-Met-Dependent Phenotypes in Vitro and Exhibits Cytoreductive Antitumor Activity in Vivo", Cancer Research, vol. 63, pp. 7345-7355 (2003).

Cooper, C.S. et al., "Amplification and overexpression of the *met* gene in spontaneously transformed NIH3T3 mouse fibroblasts", The EMBO Journal, vol. 5, No. 10, pp. 2623-2628 (1986).

Di Renzo, M.F. et al., "Overexpression and Amplification of the Met/HGF Receptor Gene during the Progression of Colorectal Cancer", Clinical Cancer Research, vol. 1, pp. 147-154 (1995).

Furge, K.A. et al., "Met receptor tyrosine kinase: enhanced signaling through adapter proteins", Oncogene, vol. 19, pp. 5582-5589 (2000).

Girgis, N.S. et al., "The Synthesis of 5-Azaindoles by Substitution-Rearrangement of 7-Azaindoles upon Treatment with Certain Primary Amines", J. Heterocyclic Chem., vol. 26, pp. 317-325 (1989).

Green, T.W. et al., Protective Groups in Organic Synthesis, $2^{nd}$ Ed., John Wiley & Sons, Inc., publ., pp. ix-x (table of contents) (1991).

Gual, P. et al., "Sustained recruitment of phospholipase C-γ to Gab1 is required for HGF-induced branching tubulogenesis", Oncogene, vol. 19, pp. 1509-1518 (2000).

Jiang, W.G. et al., "Reduction of Stromal Fibroblast-induced Mammary Tumor Growth, by Retroviral Ribozyme Transgenes to Hepatocyte Growth Factor/Scatter Factor and its Receptor, c-MET", Clinical Cancer Research, vol. 9, pp. 4274-4281 (2003).

Kenworthy, P. et al., "The presence of scatter factor in patients with metastatic spread to the pleura", Br. J. Cancer, vol. 66, pp. 243-247 (1992).

Lai, J.-F. et al., "Involvement of Focal Adhesion Kinase in Hepatocyte Growth Factor-induced Scatter of Madin-Darby Canine Kidney Cells", The Journal of Biological Chemistry, vol. 275, No. 11, pp. 7474-7480 (2000).

Lee, J.-H. et al., "A novel germ line juxtamembrane *Met* mutation in human gastric cancer", Oncogene, vol. 19, pp. 4947-4953 (2000).

Lubensky, I.A. et al., "Hereditary and Sporadic Papillary Renal Carcinomas with c-*met* Mutations Share a Distinct Morphological Phenotype", American Journal of Pathology, vol. 155, No. 2, pp. 517-526 (1999).

Masuya, D. et al., "The tumour-stromal interaction between intratumoral c-Met and stromal hepatocyte growth factor associated with tumour growth and prognosis in non-small-cell lung cancer patients", British Journal of Cancer, vol. 90, pp. 1555-1562. (2004).

Matsumoto, K. et al., "Hepatocyte Growth Factor: Molecular Structure, Roles in Liver Regeneration, and Other Biological Functions", Critical Reviews in Oncogenesis, vol. 3, Nos. 1,2, pp. 27-54 (1992).

Montesano, R. et al., "Identification of a Fibroblast-Derived Epithelial Morphogen as Hepatocyte Growth Factor", Cell, vol. 67, pp. 901-908 (1991).

Park, M. et al., "Sequence of *MET* protooncogene cDNA has features characteristic of the tyrosine kinase family of growth-factor receptors", Proc. Natl. Acad. Sci. USA, vol. 84, pp. 6379-6383 (1987).

Quintela, J.M. et al., "A Ready One-pot Preparation for Pyrrolo[2,1-*f*][1,2,4]triazine and Pyrazolo[5,1-*c*]pyrimido[4,5-*e*][1,2,4]triazine Derviatives", Tetrahedron, vol. 52, No. 8, pp. 3037-3048 (1996).

Rong, S. et al., "Met Expression and Sarcoma Tumorigenicity", Cancer Research, vol. 53, pp. 5355-5360 (1993).

Rong, S. et al., "Met Proto-oncogene Product Is Overexpressed in Tumors of p53-deficient Mice and Tumors of Li-Fraumeni Patients", Cancer Research, vol. 55, pp. 1963-1970 (1995).

Sachs, M. et al., "Essential Role of Gab1 for Signaling by the c-Met Receptor In Vivo", The Journal of Cell Biology, vol. 150, No. 6, pp. 1375-1384 (2000).

Scarpino, S. et al., "Hepatocyte Growth Factor (HGF) Stimulates Tumour Invasiveness in Papillary Carcinoma of the Thyroid", Journal of Pathology, vol. 189, pp. 570-575 (1999).

Schaeper, U. et al., "Coupling of Gab1 to c-Met, Grb2, and Shp2 Mediates Biological Responses", The Journal of Cell Biology, vol. 149, No. 7, pp. 1419-1432 (2000).

Soman, N.R. et al., "The *TPR-MET* oncogenic rearrangement is present and expressed in human gastric carcinoma and precursor lesions", Proc. Natl. Acad. Sci. USA, vol. 88, pp. 4892-4896 (1991).

Sonnenberg, E. et al., "Scatter Factor/Hepatocyte Growth Factor and Its Receptor, the c-met Tyrosine Kinase, Can Mediate a Signal Exchange between Mesenchyme and Epithelia during Mouse Development", The Journal of Cell Biology, vol. 123, No. 1, pp. 223-235 (1993).

Stabile, L.P. et al., "Inhibition of human non-small cell lung tumors by a c-Met antisense/U6 expression plasmid strategy", Gene Therapy, vol. 11, pp. 325-335 (2004).

Stella, M.C. et al., "HGF: a multifunctional growth factor controlling cell scattering", The International Journal of Biochemistry & Cell Biology, vol. 31, pp. 1357-1362 (1999).

Stoker, M. et al., "Scatter factor is a fibroblast-derived modulator of epithelial cell mobility", Nature, vol. 327, pp. 239-242 (1987).

Stuart, K.A. et al., "Hepatocyte growth factor/scatter factor-induced intracellular signalling", International Journal of Experimental Pathology, vol. 81, pp. 17-30 (2000).

Takayama, H. et al., "Diverse tumorigenesis associated with aberrant development in mice overexpressing hepatocyte growth factor/scatter factor", Proc. Natl. Acad. Sci. USA, vol. 94, pp. 701-706 (1997).

Tanimura, S. et al., "Activation of the 41/43 kDa mitogen-activated protein kinase signaling pathway is required for hepatocyte growth factor-induced cell scattering", Oncogene, vol. 17, pp. 57-65 (1998).

Barker, J.M. et al., "Thienopyridines. Part 7. Some Electrophilic Substitution Reactions of Thieno[2,3-*b*]- and -[3,2-*b*]pyridine Isosteres of 4-Oxygenated and 2,4-Dioxygenated Quinolines", J. Chem. Research (S), pp. 122-123 (1986).

Bryant, R.D. et al., "A Large Scale Synthesis of 3-Chloro-5-methoxypyridazine", J. Heterocyclic Chem., vol. 32, pp. 1473-1476 (1995).

Burckhalter, J.H. et al., "Aminoalkylphenols as Antimalarials. II. (Heterocyclic-amino)-α-amino-*o*-cresols. The Synthesis of Camoquin", J. Am. Chem. Soc., vol. 70, pp. 1363-1373 (1948).

Cañibano, V. et al., "Mild Regioselective Halogenation of Activated Pyridines with *N*-Bromosuccinimide", Synthesis, vol. 14, pp. 2175-2179 (2001).

Cheng, C.C. et al., "Potential Purine Antagonists. XII. Synthesis of 1-Alkyl(aryl)-4,6-disubstituted Pyrazolo[3,4-*d*]pyrimidines", J. Org. Chem., vol. 23, pp. 852-861 (1958).

Chi, S.-M. et al., "Palladium-catalyzed functionalization of 5- and 7-azaindoles", Tetrahedron Letters, vol. 41, pp. 919-922 (2000).

Chung, H.-A. et al., "Direct Functionalization of 4,5-Dichloropyridazin-6-one", J. Heterocyclic Chem., vol. 36, pp. 905-910 (1999).

Dorn, H. et al., "Unambiguous Synthesis of 4,7-Dihydro-4-oxo-1H-pyrazolo[3,4-b]pyridine—Further Comments on the '(N-C)-Rearrangement' of (2-Alkoxycarbonyl-vinyl-amino)pyrazols", J. Prakt. Chem., vol. 324, No. 4, pp. 557-562 (1982).

Frey, L.F. et al., "Practical routes toward the synthesis of 2-halo- and 2-alkylamino-4-pyridinecarboxaldehydes", Tetrahedron Letters, vol. 42, pp. 6815-6818 (2001).

Gemma, S. et al., "Polycondensed heterocycles. Part 12: An approach to the synthesis of 2-acetyl-1'-methyl-1,2,3,4-tetrahydrospiro-[isoquinoline-1,4'-pyrrolidine]-2'-one", Tetrahedron, vol. 58, pp. 3689-3692 (2002).

Gero, T.W. et al., "Halogenation of 2-Hydroxynicotinic Acid", Synthetic Communications, vol. 19, Nos. 3&4, pp. 553-559 (1989).

Hamdouchi, C. et al., "Imidazo[1,2-*b*]pyridazines, Novel Nucleus with Potent and Broad Spectrum Activity against Human Picornaviruses: Design, Synthesis, and Biological Evaluation", J. Med. Chem., vol. 46, No. 20, pp. 4333-4341 (2003).

Itoh, T. et al., "Studies on the Chemical Synthesis of Potential Antimetabolites. 30. Regioselective Introduction of a Chlorine Atom into the Imidazo[4,5-*b*]pyridine Nucleus", J. Heterocyclic Chem., vol. 19, pp. 513-517 (1982).

Kirk, K.L., "Synthesis of Ring-Fluorinated Serotonins and Melatonins", J. Heterocyclic Chem., vol. 13, pp. 1253-1256 (1976).

Kitamura, C. et al., "Synthesis and reactions of 3,3'-dibromodihydrodipyrrins", J. Chem. Soc. Perkin Trans. 1, pp. 1443-1447 (1997).

Koch, V. et al., "Chemistry of 3-Hydroxypyridine Part 2: Synthesis of 5,6-Dihalo-3-hydroxypyridines", Synthesis, pp. 499-501 (1990).

Morrill, C. et al., "Synthesis of Functionalized Vinyl Boronates via Ruthenium-Catalyzed Olefin Cross-Metathesis and Subsequent Conversion to Vinyl Halides", J. Org. Chem., vol. 68, No. 15, pp. 6031-6034 (2003).

Nicolaou, I. et al., "[1-(3,5-Difluoro-4-hydroxyphenyl)-1*H*-pyrrol-3-yl]-phenylmethanone as a Bioisostere of a Carboxylic Acid Aldose Reductase Inhibitor", J. Med. Chem., vol. 47, No. 10, pp. 2706-2709 (2004).

Sanghvi, Y.S. et al., "Synthesis and Biological Evaluation of Certain C-4 Substituted Pyrazolo[3,4-*b*]pyridine Nucleosides", J. Med. Chem., vol. 32, No. 5, pp. 945-951 (1989).

Schaus, J.M. et al., "Synthesis and Structure-Activity Relationships of Potent and Orally Active 5-HT$_4$ Receptor Antagonists: Indazole and Benzimidazolone Derivatives", J. Med. Chem., vol. 41, No. 11, pp. 1943-1955 (1998).

Tabanella, S. et al., "Preparation of enantiomerically pure pyridyl amino acids from serine", Org. Biomol. Chem., vol. 1, pp. 4254-4261 (2003).

Tedder, M.E. et al., "Structure-based design, synthesis, and antimicrobial activity of purine derived SAH/MTA nucleosidase inhibitors", Bioorganic & Medicinal Chemistry Letters, vol. 14, pp. 3165-3168 (2004).

Temple, Jr., C. et al., "Preparation and Properties of Some Isomeric *v*-Triazolopyridines. 1- and 3-Deaza-8-azapurines", J. Org. Chem., vol. 37, No. 23, pp. 3601-3604 (1972).

Thibault, C. et al., "Concise and Efficient Synthesis of 4-Fluoro-1*H*-pyrrolo[2,3-*b*]pyridine", Organic Letters, vol. 5, No. 26, pp. 5023-5025 (2003).

Zhang, Z. et al., "A General Method for the Preparation of 4- and 6-Azaindoles", J. Org. Chem., vol. 67, pp. 2345-2347 (2002).

U.S. Appl. No. 11/292,358, filed Dec. 1, 2005, Borzilleri et al.

Database Crossfire Beilstein Beilstein Institut zur Foerderung der Chemischen Wissenschaft, Frankfurt am Main, DE; XP002362294 Database accession No. BRN 667921.

Database Crossfire Beilstein Beilstein Institut zur Foerderung der Chemischen Wissenschaft, Frankfurt am Main, DE; XP002362295 Database accession No. BRN 413351.

Database Crossfire Beilstein Beilstein Institut zur Foerderung der Chemischen Wissenschaft, Frankfurt am Main, DE; XP002362296 Database accession No. BRN 450834.

Database Crossfire Beilstein Beilstein Institut zur Foerderung der Chemischen Wissenschaft, Frankfurt am Main, DE; XP002362297 Database accession No. BRN 448780.

U.S. Appl. No. 11/406,795, filed Apr. 9, 2006, Borzilleri et al.

BICYCLIC HETEROCYCLES AS KINASE INHIBITORS

RELATED APPLICATIONS

This application claims priority benefit under Title 35 § 119(e) of U.S. provisional Application No. 60/565,381, filed Apr. 26, 2004, the contents of which are herein incorporated by reference.

FIELD OF THE INVENTION

This invention relates to compounds that inhibit the protein tyrosine kinase activity of growth factor receptors such as c-Met, thereby making them useful as anti-cancer agents. The pharmaceutical compositions that comprise these compounds are also useful in the treatment of diseases, other than cancer, which are associated with signal transduction pathways operating through growth factor and anti-angiogenesis receptors such as c-Met.

BACKGROUND OF THE INVENTION

Hepatocyte growth factor (HGF), also known as scatter factor (SF), because of its ability to disrupt colony formation in vitro, is a mesenchymally derived cytokine known to induce multiple pleiotropic responses in normal and neoplastic cells (Sonnenberg et al., *J. Cell Biol.* 123:223-235, 1993; Matsumato et al., *Crit. Rev. Oncog.* 3:27-54,1992; and Stoker et al., *Nature* 327:239-242, 1987). These responses are known to include proliferation in both epithelial and endothelial cells, dissociation of epithelial colonies into individual cells, stimulation of motility (motogenesis) of epithelial cells, cell survival, induction of cellular morphogenesis (Montesano et al., *Cell* 67:901-908, 1991), and promotion of invasion (Stella et al., *Int. J. Biochem. Cell Biol.* 12:1357-62, 1999 and Stuart et al., *Int. J. Exp. Path.* 81:17-30, 2000), all critical processes underlying metastasis. HGF has also been reported to promote angiogenesis (Bussolino et al., *J. Cell Biol.* 119:629-641, 1992). In addition, HGF plays a critical role in tissue regeneration, wound healing, and normal embryonic processes, all of which are dependent on both cell motility and proliferation.

HGF initiates these physiological processes through high affinity binding to its cognate receptor, the Met protein tyrosine kinase receptor, an identified protooncogene (Park et al., *Proc. Natl. Acad. Sci. USA* 84:6379-83, 1987 and Bottaro et al., *Science* 251:802-4, 1991). The mature form of Met consists of a highly glycosylated external α-subunit as well as a β-subunit with a large extracellular domain, a transmembrane segment and a cytoplasmic tyrosine kinase domain. Ligand engagement induces Met dimerization that results in an autophosphorylated activated receptor. Activation of Met promotes signal transduction cascades as defined by transphosphorylation of key cytoplasmic tyrosine residues responsible for recruiting multiple effector proteins (Furge et al., *Oncogene* 19:5582-9, 2000). These include the p85 subunit of the PI3-kinase, phospholipase Cγ (Gaul et al., *Oncogene* 19:1509-18, 2000), Grb2 and Shc adaptor proteins, the protein phosphatase SHP2 and Gab1. The latter adapter has emerged as the major downstream docking molecule that becomes tyrosine phosphorylated in response to ligand occupancy (Schaeper et al., *J. Cell Biol.* 149:1419-32, 2000; Bardelli, et al., *Oncogene* 18:1139-46, 1999 and Sachs et al., *J. Cell Biol.* 150:1375-84, 2000). Activation of other signaling molecules has been reported in HGF stimulated cells, most notably Ras, MAP kinases, STATs, ERK-1, -2 and FAK (Tanimura et al., *Oncogene* 17:57-65,1998; Lai et al., *J. Biol. Chem.* 275:7474-80 2000 and Furge et al., *Oncogene* 19:5582-9, 2000). The role of many of these signaling molecules has been well established in cell proliferation.

Met, also referred to as hepatocyte growth factor receptor (HGFR), is expressed predominantly in epithelial cells but has also been identified in endothelial cells, myoblasts, hematopoietic cells and motor neurons. Overexpression of HGF and activation of Met has been associated with the onset and progression in a number of different tumor types as well as in the promotion of metastatic disease. Initial evidence linking Met to cancer has been supported by the identification of kinase domain missense mutations, which predisposes individuals to papillary renal carcinomas (PRC) and hepatocellular carcinomas (HCC) (Lubensky et al., *Amer. J. Pathology,* 155:517-26, 1999). Mutated forms of Met have also been identified in ovarian cancer, childhood HCC, gastric carcinoma, head and neck squamous cell carcinoma, non-small cell lung carcinoma, colorectal metastasis (Christensen et al., *Cancer Res.,* 63:7345-55, 2003; Lee et al., *Oncogene,* 19:4947-53, 2000 and Direnzo et al., *Clin. Cancer Res.,* 1:147-54, 1995). In addition, further evidence supporting the role of the Met in cancer is based on the overexpression of HGF and Met receptor in various tumors including thyroid, ovarian and pancreatic carcinomas. It has also been demonstrated to be amplified in liver metastases of colorectal carcinomas (Rong et al. *Cancer Res.* 55:1963-1970, 1995; Rong et al., *Cancer Res.* 53:5355-5360, 1993; Kenworthy et al., *Br. J. Cancer* 66:243-247, 1992 and Scarpino et al. *J. Pathology* 189:570-575, 1999). TPR-Met (an activated form similar to BCR/Abl in CML) has been described and identified in human gastric carcinoma (PNAS 88:4892-6, 1991). In patients with invasive breast carcinoma and in a recent study in non small cell lung cancer patients, expression of either the receptor or ligand is a predictor of decreased survival, further linking Met to tumor progression (Camp et al., *Cancer* 86:2259-65 1999 and Masuya et al., *Br. J. Cancer,* 90:1555-62, 2004). In general, most human tumors and tumor cell lines of mesenchymal origin inappropriately express HGFR and/or HGF.

Numerous experimental data support the role of HGF and Met in tumor invasion, growth, survival and progression ultimately leading to metastases. Preclinically, transgenic expression of HGF results in a metastatic phenotype (Takayama et al., *PNAS,* 94:701-6, 1997) and an amplified/overexpressed Met spontaneously transforms NIH-3T3 cells (Cooper et al., *EMBO J.,* 5:2623-8, 1986).

Biological agents, such as ribozymes, antibodies and antisense RNA targeting either HGF or Met have been shown to inhibit tumorogenesis (Stabile et al., *Gene Therapy,* 11:325-35, 2004, Jiang et al., *Clin. Cancer Res,* 9:4274-81, 2003 and Genentech U.S. Pat. No. 6,214,344, 2001). Thus, selective, small molecule kinase modulators targeting Met are expected to have therapeutic potential for the treatment of cancers in which Met receptor activation plays a critical role in the development and progression of primary tumors and secondary metastases. HGF is also known to regulate angiogenesis, a process critical in tumor growth and dissemination. Therefore, there is a potential for this class of modulators to impact angiogenesis-dependent diseases as well that may include among others, diabetic retinopathy, macular degeneration, obesity and inflammatory disease such as rheumatoid arthritis.

SUMMARY OF THE INVENTION

The invention comprises compounds that are useful for treating cancer having Formula I or II:

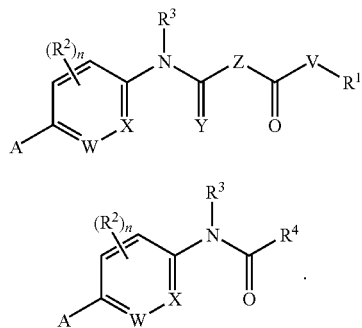

and includes their enantiomers, diastereomers, pharmaceutically acceptable salts, prodrugs and solvates thereof, wherein:

$R^1$ is selected from the group consisting of H, alkyl, substituted alkyl, alkenyl, substituted alkenyl, alkynyl, substituted alkynyl, cycloalkyl, substituted cycloalkyl, heterocloalkyl, substituted heterocycloalkyl, aryl, substituted aryl, aralkyl, substituted aralkyl, heteroaryl, substituted heteroaryl, heteroarylalkyl, and substituted heteroarylalkyl;

$R^2$ is selected from the group consisting of H, halogen, cyano, $NO_2$, $OR^5$, $NR^6R^7$, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, arylalkyl, substituted arylalkyl, heterocloalkyl, and substituted heterocycloalkyl;

V is $CH_2$ or $NR^8$;

W and X are independently CH or N;

Y is O, S, or $NR^9$;

Z is $-CR^{10}OR^{11}-$, or $-(CR^{10}R^{11})_m NR^{12}-$;

m is 0 to 2;

A is:

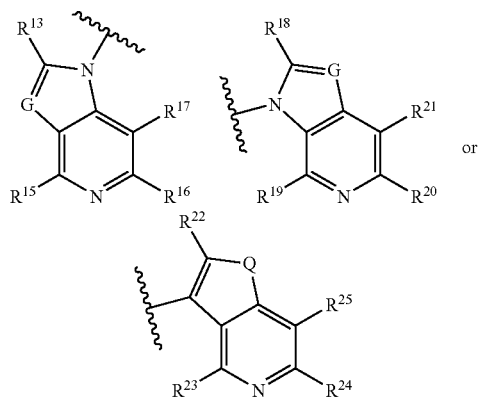

wherein

G is $CR^{14}$ or N;

Q is O or $NR^{26}$;

$R^3$, $R^5$, $R^5$, $R^6$, $R^7$, $R^8$ and $R^{12}$ are independently H, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocloalkyl, or substituted heterocycloalkyl;

$R^9$ is H, alkyl, substituted alkyl, CN, $NO_2$ or $SO_2$amino;

$R^{10}$ and $R^{11}$ are independently H, halogen, alkyl, substituted alkyl, cycloalkyl, substituted cycloalkyl, aryl, substituted aryl, heteroaryl, substituted heteroaryl, heterocloalkyl, substituted heterocycloalkyl, or taken together to form a carbocyclic or heterocyclic ring having from 3 to 8 atoms;

$R^{13}$, $R^{15}$, $R^{16}$, $R^{17}$, $R^{18}$, $R^{19}$, $R^{20}$, $R^{21}$, $R^{22}$, $R^{23}$, $R^{24}$ $R^{25}$ are independently selected from the group consisting of H, halogen, $NR^{27}R^{28}$, $OR^{29}$, $CO_2R^{30}$, $CO_2NR^{31}R^{32}$, $SO_2R^{33}$, alkyl, substituted alkyl, alkenyl, substituted alkenyl, cycloalkyl, substituted cycloalkyl, heterocycloalkyl, substituted heterocycloalkyl, aryl, substituted aryl, optionally substituted aralkyl, alkoxyalkyl, heteroaryl, substituted heteroaryl, and heterocycloalkylalkyl;

$R^{14}$ is H, halogen, $NR^{27}R^{28}$, $COR^{30}$, $CONR^{31}R^{32}$, $SO_2R^{33}$, alkyl, substituted alkyl, cycloalkyl, substituted cycloalkyl, aryl, substituted aryl, heteroaryl, substituted heteroaryl, heterocycloalkyl, or substituted heterocycloalkyl;

$R^{26}$, $R^{27}$, $R^{28}$, $R^{29}$, $R^{30}$, $R^{31}$, $R^{32}$ and $R^{33}$ are each independently H, alkyl, substituted alkyl, cycloalkyl, substituted cycloalkyl, aryl, substituted aryl, heteroaryl, substituted heteroaryl, heterocycloalkyl, or substituted heterocycloalkyl.

According to one embodiment of the present invention, Y is O or S.

According to one embodiment of the present invention, A is one of:

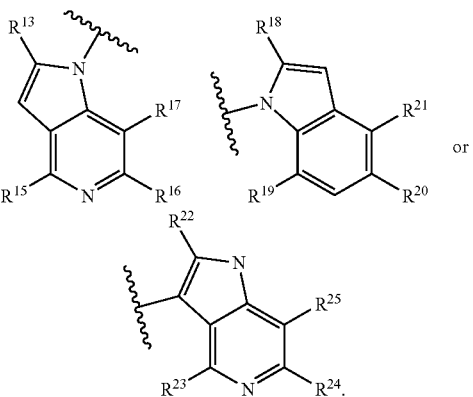

According to one embodiment of the present invention, $R^2$ and $R^3$ are H.

According to one embodiment of the present invention, V is NH and Z is $CH_2$.

In yet another embodiment, V is $CH_2$ and Z is NH.

According to some embodiments of the present invention, $R^1$ is phenyl, for example a halo substituted phenyl, such as fluorophenyl. In other embodiments, $R^1$ is an optionally substituted $C_1$ to $C_6$ alkyl, or a $C_3$ to $C_7$ cycloalkyl.

In one embodiment of the present invention, $R^4$ is a phenyl or pyridyl group, optionally substituted with an oxo or phenyl group. In other embodiments, $R^4$ can be a pyrazole or a pyrrolidine group.

In one embodiment of the present invention the pyridyl group is an N-oxide pyridyl.

In preferred embodiments of the present invention, the compounds have $IC_{50}$ values of less than about 1.0 µM.

The present invention also provides methods for treating a proliferative disease, such as cancer, by administering to a mammalian species in need of such treatment a pharmaceutically effective amount of a compound having either Formula I or II as defined above.

The present invention also provides a pharmaceutical product comprising:
(a) a container;
(b) a pharmaceutical composition contained therein wherein said composition comprises a compound having either Formula I or II, as defined above; and
(c) a package insert that indicates that the pharmaceutical composition can be used for the treatment of cancer.

DESCRIPTION OF THE INVENTION

The present invention provides for compounds of Formulas I and II as defined above, pharmaceutical compositions employing such compounds, and methods of using such compounds for the treatment of cancer.

Listed below are definitions of various terms used to describe the compounds of the instant invention. These definitions apply to the terms as they are used throughout the specification (unless they are otherwise limited in specific instances) either individually or as part of a larger group.

The term "alkyl" herein alone or as part of another group refers to a monovalent alkane (hydrocarbon) derived radical containing from 1 to 12 carbon atoms unless otherwise defined. An alkyl group is an optionally substituted straight, branched or cyclic saturated hydrocarbon group. Alkyl groups may be substituted at any available point of attachment. An alkyl group substituted with another alkyl group is also referred to as a "branched alkyl group". Exemplary alkyl groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the like. Exemplary substituents include but are not limited to one or more of the following groups: alkyl, cycloalkyl, heterocycloalkyl, aryl, heteroaryl, halo (such as F, Cl, Br, I), haloalkyl (such as $CCl_3$ or $CF_3$), alkoxy, alkylthio, hydroxy, carboxy (—COOH), alkyloxycarbonyl (—C(O)R), alkylcarbonyloxy (—OCOR), amino (—$NH_2$), carbamoyl (—NHCOOR— or —OCONHR—), urea (—NHCONHR—) or thiol (—SH).

The term "alkenyl" herein alone or as part of another group refers to a hydrocarbon radical straight, branched or cyclic containing from 2 to 12 carbon atoms and at least one carbon to carbon double bond. Alkenyl groups may also be substituted at any available point of attachment. Exemplary substituents for alkenyl groups include those listed above for alkyl groups.

The term "alkynyl" herein alone or as part of another group refers to a hydrocarbon radical straight, branched or cyclic containing from 2 to 12 carbon atoms and at least one carbon to carbon triple bond. Alkynyl groups may also be substituted at any available point of attachment. Exemplary substituents for alkynyl groups include those listed above for alkyl groups.

The numbers in the subscript after the symbol "C" define the number of carbon atoms a particular group can contain. For example "$C_{1-6}$alkyl" means a straight or branched saturated carbon chain having from one to six carbon atoms; examples include methyl, ethyl, n-propyl, isopropyl, n-butyl, sec-butyl, isobutyl, t-butyl, n-pentyl, sec-pentyl, isopentyl, and n-hexyl. Depending on the context, "$C_{1-6}$ alkyl" can also refer to $C_{1-6}$ alkylene which bridges two groups; examples include propane-1,3-diyl, butane-1,4-diyl, 2-methyl-butane-1,4-diyl, etc. "$C_{2-6}$ alkenyl" means a straight or branched carbon chain having at least one carbon-carbon double bond, and having from two to six carbon atoms; examples include ethenyl, propenyl, isopropenyl, butenyl, isobutenyl, pentenyl, and hexenyl. Depending on the context, "$C_{2-6}$ alkenyl" can also refer to $C_{2-6}$ alkenediyl which bridges two groups; examples include ethylene-1,2-diyl (vinylene), 2-methyl-2-butene-1,4-diyl, 2-hexene-1,6-diyl, etc. "$C_{2-6}$ alkynyl" means a straight or branched carbon chain having at least one carbon-carbon triple bond, and from two to six carbon atoms; examples include ethynyl, propynyl, butynyl, and hexynyl.

The term "cycloalkyl" herein alone or as part of another group is a species of alkyl containing from 3 to 15 carbon atoms, without alternating or resonating double bonds between carbon atoms. It may contain from 1 to 4 rings. Exemplary groups include cyclopropyl, cyclobutyl, cyclopentyl, cyclohexyl, adamantyl, etc. Cycloalkyl groups may be substituted at any available point of attachment. Exemplary substituents include one or more of the following groups: halogen, such as F, Br, or Cl, hydroxyl, alkyl, alkoxy, amino, nitro, cyano, thiol, alkylthio, and any of the subsitituents described above for alkyl groups.

The term "carbocyclic ring" herein alone or as part of another group refers to stable, saturated or partially unsaturated monocyclic ring hydrocarbons of 3 to 7 carbon atoms such as cyclopropyl, cyclobutyl, cyclopentyl, cyclohexyl and cycloheptyl. The carbocyclic ring may be optionally substituted at one or more substitutable ring positions by one or more groups independently selected from hydroxyl, alkyl (preferably lower alkyl), alkoxy (preferably lower alkoxy), nitro, monoalkylamino (preferably a lower alkylamino), dialkylamino (preferably a di[lower]alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy[lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups.

The terms "alkoxy" or "alkylthio" herein alone or as part of another group denote an alkyl group as described above bonded through an oxygen linkage (—O—) or a sulfur linkage (—S—), respectively.

The term "alkyloxycarbonyl" herein alone or as part of another group denotes an alkoxy group bonded through a carbonyl group. An alkoxycarbonyl radical is represented by the formula: —C(O)OR, where the R group is a straight or branched $C_{1-6}$ alkyl group, cycloalkyl, aryl, or heteroaryl.

The term "alkylcarbonyl" herein alone or as part of another group refers to an alkyl group bonded through a carbonyl group.

The term "alkylcarbonyloxy" herein alone or as part of another group denotes an alkylcarbonyl group bonded through an oxygen linkage.

The term "aryl" herein alone or as part of another group refers to monocyclic or bicyclic aromatic rings, e.g. phenyl, substituted phenyl and the like, as well as groups which are fused, e.g., napthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. Aryl groups may optionally be substituted with one or more groups including, but not limited to halogen, alkyl, alkoxy, hydroxy, carboxy, carbamoyl, alkyloxycarbonyl, nitro, alkenyloxy, trifluoromethyl, amino, cycloalkyl, aryl, heteroaryl, cyano, alkyl $S(O)_m$ (m=0, 1, 2), or thiol.

The term "arylalkyl" or "aralkyl" herein alone or as part of another group denotes an aryl group as described above bonded through an alkyl group, as described above. And example of an aralkyl group is a benzyl group.

The term "amino" herein alone or as part of another group refers to —$NH_2$. An "amino" may optionally be substituted with one or two substituents, which may be the same or different, such as alkyl, aryl, arylalkyl, alkenyl, alkynyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl, thioalkyl carbonyl or carboxyl. These substituents may be further substituted with a carboxylic acid, any of the alkyl or aryl substituents set out herein. In some embodiments, the amino groups are substituted with carboxyl or carbonyl to form N-acyl or N-carbamoyl derivatives The term "heteroaryl" herein alone or as part of another group refers to substituted and unsubstituted aromatic 5 or 6 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents selected from the group consisting of halo, alkyl, substituted alkyl, alkenyl, alkynyl, aryl, nitro, cyano, hydroxy, alkoxy, thioalkyl, —$CO_2H$, —C(=O)H, —$CO_2$-alkyl, —C(=O)alkyl, phenyl, benzyl, phenylethyl, phenyloxy, phenylthio, cycloalkyl, substituted cycloalkyl, heterocyclo, heteroaryl, —NR'R", —C(=O)NR'R", —$CO_2$NR'R", —C(=O)NR'R", —NR'$CO_2$R", —NR'C(=O)R", —$SO_2$NR'R", and —NR'$SO_2$R", wherein each of R' and R" is independently selected from hydrogen, alkyl, substituted alkyl, and cycloalkyl, or R' and R" together form a heterocyclo or heteroaryl ring.

Exemplary monocyclic heteroaryl groups include pyrrolyl, pyrazolyl, pyrazolinyl, imidazolyl, oxazolyl, diazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxaxolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

The term "heterocyclic ring" herein alone or as part of another group refers to a stable, saturated, or partially unsaturated monocyclic ring system containing 5 to 7 ring members of carbon atoms and other atoms selected from nitrogen, sulfur and/or oxygen. Preferably, a heterocyclic ring is a 5 or 6-membered monocyclic ring and contains one, two, or three heteroatoms selected from nitrogen, oxygen and/or sulfur. The heterocyclic ring may be optionally substituted which means that the heterocyclic ring may be substituted at one or more substitutable ring positions by one or more groups independently selected from alkyl (preferably lower alkyl), alkoxy (preferably lower alkoxy), nitro, monoalkylamino (preferably a lower alkylamino), dialkylamino (preferably a di[lower]alkylamino),cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy [lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups. Examples of such heterocyclic rings are isoxazolyl, imidazolinyl, thiazolinyl, imidazolidinyl, pyrrolyl, pyrrolinyl, pyranyl, pyrazinyl, piperidyl, morpholinyl and triazolyl. The heterocyclic ring may be attached to the parent structure through a carbon atom or through any heteroatom of the heterocyclyl that results in a stable structure.

The term "heteroatom" means O, S or N, selected on an independent basis. It should be noted that any heteroatom with unsatisfied valences is assumed to have the hydrogen atom to satisfy the valences.

The term "halogen" or "halo" refers to chlorine, bromine, fluorine or iodine selected on an independent basis.

When a functional group is termed "protected", this means that the group is in modified form to preclude undesired side reactions at the protected site. Suitable protecting groups for the compounds of the present invention will be recognized from the present application taking into account the level of skill in the art, and with reference to standard textbooks, such as Greene, T. W. et al., *Protective Groups in Organic Synthesis*, Wiley, N.Y. (1991).

As used herein, the term "patient" encompasses all mammalian species.

The term "anticancer" agent includes any known agent that is useful for the treatment of cancer including the following: 17α-ethinylestradiol, diethylstilbestrol, testosterone, prednisone, fluoxymesterone, dromostanolone propionate, testolactone, megestrolacetate, methylprednisolone, methyl-testosterone, prednisolone, triamcinolone, chlorotrianisene, hydroxyprogesterone, aminoglutethimide, estramustine, medroxyprogesteroneacetate, leuprolide, flutamide, toremifene, Zoladex; matrix metalloproteinase inhibitors; VEGF inhibitors, such as anti-VEGF antibodies (Avastin,) and small molecules such as ZD6474 and SU6668; Vatalanib, BAY-43-9006, SU11248, CP-547632, and CEP-7055; Her 1 and Her 2 inhibitors including anti-Her2 antibodies (Herceptin); EGFR inhibitors including gefitinib, erlotinib, ABX-EGF, EMD72000, 11F8, and cetuximab; Eg5 inhibitors, such as SB-715992, SB-743921, and MKI-833; pan Her inhibitors, such as canertinib, EKB-569, CI-1033, AEE-788, XL-647, mAb 2C4, and GW-572016; Src inhibitors, e.g. Gleevac and BMS-354825; Casodex® (bicalutamide, Astra Zeneca), Tamoxifen; MEK-1 kinase inhibitors, MAPK kinase inhibitors, aurora kinase inhibitors, PI3 kinase inhibitors; PDGF inhibitors, such as imatinib; anti-angiogenic and anti-vascular agents which, by interrupting blood flow to solid tumors, render cancer cells quiescent by depriving them of nutrition; castration, which renders androgen dependent carcinomas non-proliferative; IGF1R inhibitors such as those disclosed in US2004/44203A1, inhibitors of non-receptor and receptor tyrosine kinases; inhibitors of integrin signaling; tubulin acting agents such as vinblastine, vincristine, vinorelbine, vinflunine, paclitaxel, docetaxel, 7-O-methylthiomethylpaclitaxel, 4-desacetyl4-methylcarbonatepaclitaxel, 3'-tert-butyl-3'-N-tert-butyloxycarbonyl-4-deacetyl-3'-dephenyl-3'-N-debenzoyl-4-O-methoxycarbonyl-paclitaxel, C-4 methyl carbonate paclitaxel, epothilone A, epothilone B, epothilone C, epothilone D, desoxyepothilone A, desoxyepothilone B, [1S-[1R*,3R*(E),7R*,10S*,11R*,12R*,16S*]]-7-11-dihydroxy-8,8,10,12,16-pentamethyl-3-[1-methyl-2-(2-methyl-4-thiazolyl)ethenyl]-4-aza-17 oxabicyclo[14.1.0]heptadecane-5,9-dione (ixabepilone), [1S-[1R*,3R*(E),7R*,10S *, 11R*,12R*,16S *]]-3-[2-[2-(aminomethyl)-4-thiazolyl]-1-methylethenyl]-7,11-dihydroxy-8,8,10,12,16-pentamethyl-4-17-dioxabicyclo[14.1.0]-heptadecane-5,9-dione, and derivatives thereof; CDK inhibitors, antiproliferative cell cycle inhibitors, epidophyllotoxin, etoposide, VM-26; antineoplastic enzymes, e.g., topoisomerase I inhibitors, camptothecin, topotecan, SN-38; procarbazine; mitoxantrone; platinum coordination complexes such as cisplatin, carboplatin and oxaliplatin; biological response modifiers; growth inhibitors; antihormonal therapeutic agents; leucovorin; tegafur; antimetabolites such as purine antagonists (e.g. 6-thioguanine and 6-mercaptopurine; glutamine antagonists, e.g. DON (AT-125; d-oxo-norleucine); ribonucleotide reductase inhibitors; mTOR inhibitors; and haematopoietic growth factors.

Additional cytotoxic agents include, cyclophosphamide, doxorubicin, daunorubicin, mitoxanthrone, melphalan, hexamethyl melamine, thiotepa, cytarabin, idatrexate, trimetrexate, dacarbazine, L-asparaginase, bicalutamide, leuprolide, pyridobenzoindole derivatives, interferons, and interleukins.

Suitable examples of salts of the compounds according to the invention with inorganic or organic acids are hydrochloride, hydrobromide, sulfate, methanesulfonate, maleate, fumarate, and phosphate. Salts which are unsuitable for pharmaceutical uses but which can be employed, for example, for the isolation or purification of free compounds I or II, their pharmaceutically acceptable salts, are also included.

In general, the instant invention comprises a compound having Formula I or II

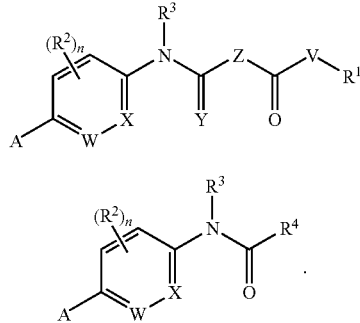

including their enantiomers, diastereomers, pharmaceutically acceptable salts, prodrugs and solvates thereof, wherein:

$R^1$ is selected from the group consisting of H, alkyl, substituted alkyl, alkenyl, substituted alkenyl, alkynyl, substituted alkynyl, cycloalkyl, substituted cycloalkyl, heterocycloalkyl, substituted heterocycloalkyl, aryl, substituted aryl, aralkyl, substituted aralkyl, heteroaryl, substituted heteroaryl, heteroarylalkyl, and substituted heteroarylalkyl;

$R^2$ is selected from the group consisting of H, halogen, cyano, $NO_2$, $OR^5$, $NR^6R^7$, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, aryalkyl, substituted arylalkyl, heterocycloalkyl, and substituted heterocycloalkyl;

V is $CH_2$ or NR8;

W and X are independently C or N;

Y is O, S, or $NR^9$;

Z is $-CR^{10}R^{11}-$, or $-(CR^{10}R^{11})_mNR^{12}-$;

m is 0to2;

A is:

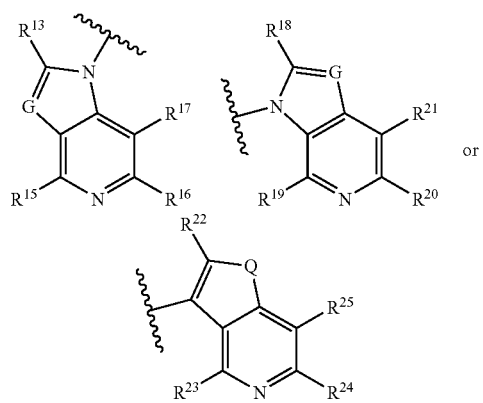

wherein

G is $CR^{14}$ or N;

Q is O or $NR^{26}$;

$R^3$, $R^4$, $R^5$, $R^6$, $R^7$, $R^8$ and $R^2$ are independently H, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocycloalkyl, or substituted heterocycloalkyl;

$R^9$ is H, alkyl, substituted alkyl, CN, $NO_2$ or $SO_2$Amino;

$R^{10}$ and $R^{11}$ are independently H, halogen, alkyl, substituted alkyl, cycloalkyl, substituted cycloalkyl, aryl, substituted aryl, heteroaryl, substituted heteroaryl, heterocycloalkyl, substituted heterocycloalkyl, or taken together to form a carbocyclic or heterocyclic ring having from 3 to 8 atoms;

$R^{13}$, $R^{15}$, $R^{16}$, $R^{17}$, $R^{18}$, $R^{19}$, $R^{20}$, $R^{21}$, $R^{22}$, $R^{23}$, $R^{24}$ and $R^{25}$ are independently selected from the group consisting of H, halogen, $NR^{27}R^{28}$, $OR^{29}$, $CO_2R^{30}$, $CO_2NR^{31}R^{32}$, $SO_2R^{33}$, alkyl, substituted alkyl, alkenyl, substituted alkenyl, cycloalkyl, substituted cycloalkyl, heterocycloalkyl, substituted heterocycloalkyl, aryl, substituted aryl, optionally substituted aralkyl, alkoxyalkyl, heteroaryl, substituted heteroaryl, and heterocycloalkylalkyl;

$R^{14}$ is H, halogen, $NR^{27}R^{28}$, $COR^{30}$, $CONR^{31}R^{32}$, $SO_2R^{33}$, alkyl, substituted alkyl, cycloalkyl, substituted cycloalkyl, aryl, substituted aryl, heteroaryl, substituted heteroaryl, heterocycloalkyl, or substituted heterocycloalkyl;

$R^{26}$, $R^{27}$, $R^{28}$, $R^{29}$, $R^{30}$, $R^{31}$, $R^{32}$ and $R^{33}$ are each independently H,alkyl, substituted alkyl, cycloalkyl, substituted cycloalkyl, aryl, substituted aryl, heteroaryl, substituted heteroaryl, heterocycloalkyl, or substituted heterocycloalkyl.

The invention further provides a pharmaceutical composition comprising compounds of Formulas I or II, as defined above, and a pharmaceutically acceptable carrier. Optionally, the pharmaceutical carrier may further comprise at least one other anti-cancer agent formulated as a fixed dose.

The invention also provides a method for treating a proliferative disease via modulation of Met kinase by administering to a mammalian species in need of such treatment an effective amount of a compound of formulas I or II, as defined above. In another embodiment, the invention provides a method for treating a proliferative disease via modulation of Met kinase by administering to a mammalian species in need of such treatment an effective amount of a compound of formula I or II, as defined above, in combination (simultaneously or sequentially) with at least one other anti-cancer agent. In a preferred embodiment, the proliferative disease is cancer.

Certain compounds of Formulas I and II may generally be prepared according to the following Schemes 1-4. Solvates (e.g., hydrates) of the compounds of Formulas I and II are also within the scope of the present invention. Methods of solvation are generally known in the art. Accordingly, the compounds of the instant invention may be in the free or hydrate form, and may be obtained by methods exemplified by the following schemes below.

Azaindole derivatives 4 and 11 can be prepared using the synthetic routes outlined in Schemes 1 and 2. For example, heating 4-chloro-1H-pyrrolo[2,3-b]pyridine (see, the methods generally disclosed in 1, Cheng, C.-C. et al. *J. Physical Chem.* 2003, 107, 1459-1471, herein incorporated by reference) in the presence of an appropriately substituted aniline 2 (See, generally, Girgis, N. S. et al. *J. Heterocyclic Chem.* 1989, 26, 317-325, herein incorporated by reference) can provide the rearrangement product 3 (Scheme 1). Protection of the amine moiety of 3 with, for example di-tert-butyl dicarbonate followed by reduction of the nitro group with zinc dust and ammonium chloride in a THF-MeOH mixture can afford the Boc-protected aniline 4. Desired compounds 5 and 6 can then be prepared by acylation of aniline 5 with, for example isocyanates, acid chlorides or by treatment with a carboxylic acid and a coupling reagent, such as: benzotriazol-1-yloxytris(trimethylamino)phosphonium hexafluorophosphate (BOP reagent), bromotripyrrolidinophosphonium hexafluorophosphate (PyBrOP), O—(1H-benzotriazol-1-yl)-N,N,N',N'-tetramethyluronium tetrafluoroborate (TBTU), followed by a deprotection step using acidic conditions. Formation of the acylthiourea of 5 (Y═S, Z═NH) can be accomplished by treating aniline 5 with an appropriately substituted isothiocyanate followed by the deprotection step.

SCHEME 1

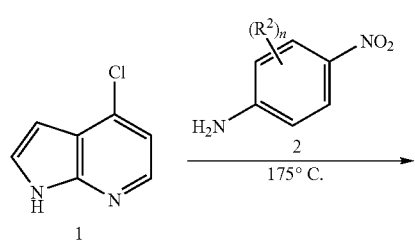

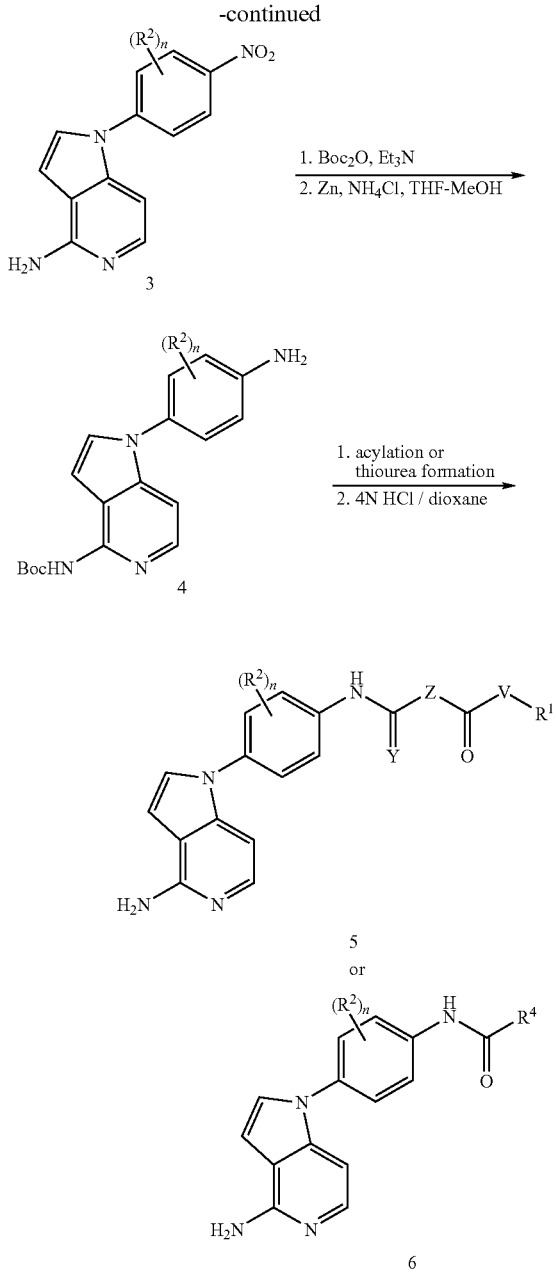

The thermally promoted rearrangement of 4-chloro-1H-pyrrolo[2,3-b]pyridine (1) can also be carried out in the presence of benzylamine to provide amine 7 (Scheme 2). Removal of the benzyl group under hydrogenation conditions with Pearlman's catalyst (Pd(OH)$_2$/C) followed by treatment of the intermediate with di-tert-butyl dicarbonate and triethylamine can furnish Boc-protected aminoazaindole 8. Treatment of 8 with N-chlorosuccinimide (NCS) or N-bromosuccinimide (NBS) can provide the halogenated intermediate 9. Cross-coupling of compound 9 with, for example boronic acid 10 in the presence of a palladium(0) catalyst, followed by reduction of the nitro intermediate with catalytic hydrogenation can afford aniline 11. Intermediate 11 can be processed in a similar manner as described above to provide the azaindole compounds 12 and 13.

SCHEME 2

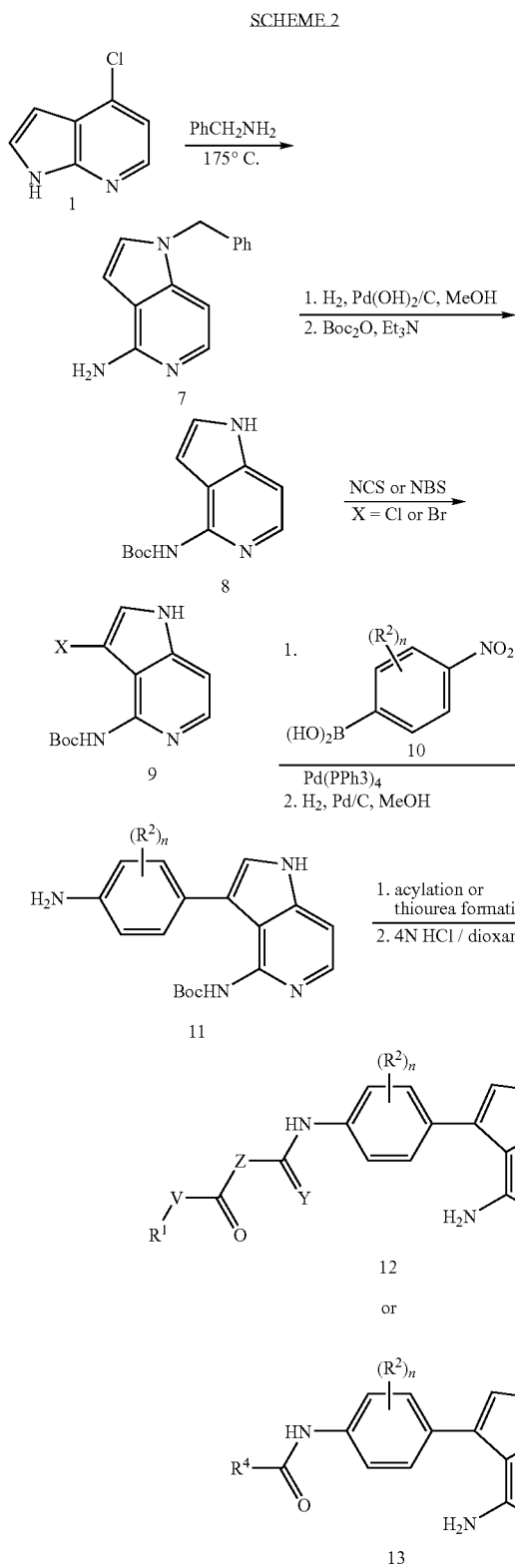

tert-butyl 4-aminopicolinate (15) using a two step procedure involving sodium azide in DMSO at elevated temperatures followed by triphenylphosphine in a mixture of THF-H$_2$O. Bromination of compound 15 with N-bromosuccinimide (NBS) in CH$_2$Cl$_2$ or dichloroethane followed by acylation of the amine intermediate with ethyl chloroformate can provide tert-butyl 5-bromo-4-(ethoxycarbonyl)picolinate (16). Coupling of pyridine derivative 16 with trimethylsilylacetylene in the presence of a palladium catalyst, copper iodide and triethylamine can provide intermediate 17 which can then be cyclized with tetrabutylammonium fluoride to generate tert-butyl 1H-pyrrolo[3,2-c]pyridine-6-carboxylate (18). Combining azaindole 18 with benzene derivative 19 in the presence of a base, such as sodium hydride can provide intermediate 20. Acid promoted hydrolysis of compound 20 using trifluoroacetic acid in methylene chloride followed by Curtius rearrangement with diphenylphosphoryl azide (DPPA) in the presence of t-butanol can afford the N-Boc protected intermediate 21. Reduction of the nitro moiety of compound 21 with zinc dust and ammonium chloride in a THF-MeOH mixture can provide compound 22. Acylation or acylurea formation of intermediate 22 followed by removal of the N-Boc protecting group can be accomplished using chemistry previously described in Scheme 1 to generate the desired azaindole derivatives 23 and 24.

SCHEME 3

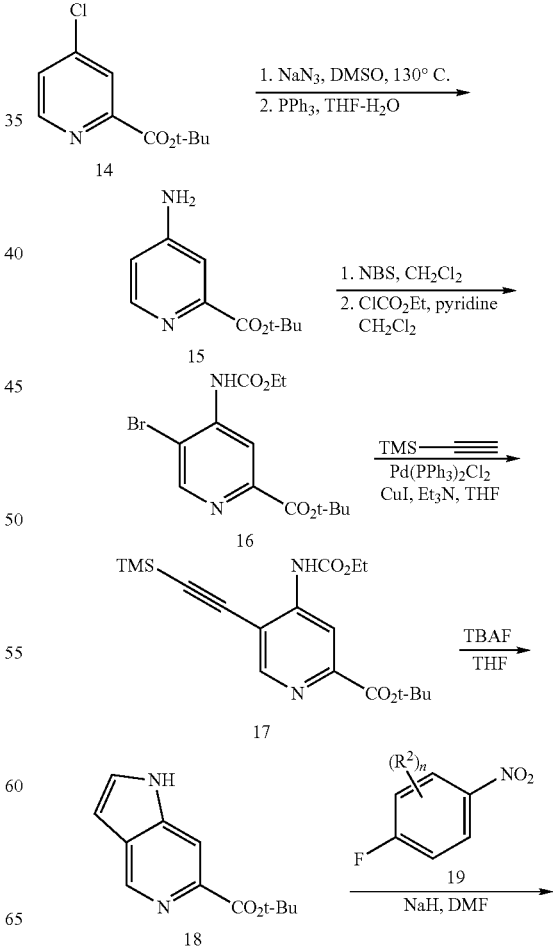

Azaindole derivatives 23 and 24 can be prepared using the synthetic route outlined in Scheme 3. For example, tert-butyl 4-chloropicolinate (14), derived from picolinic acid (Aldrich) using known chemistry (cf. Example 5), can be converted to

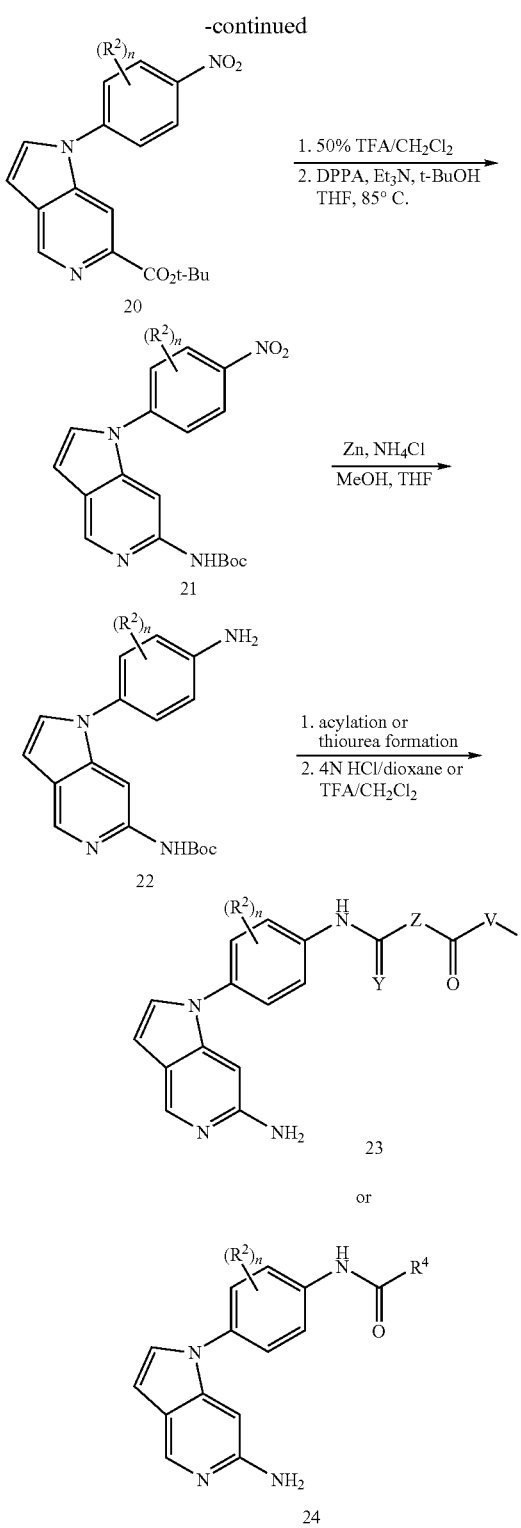
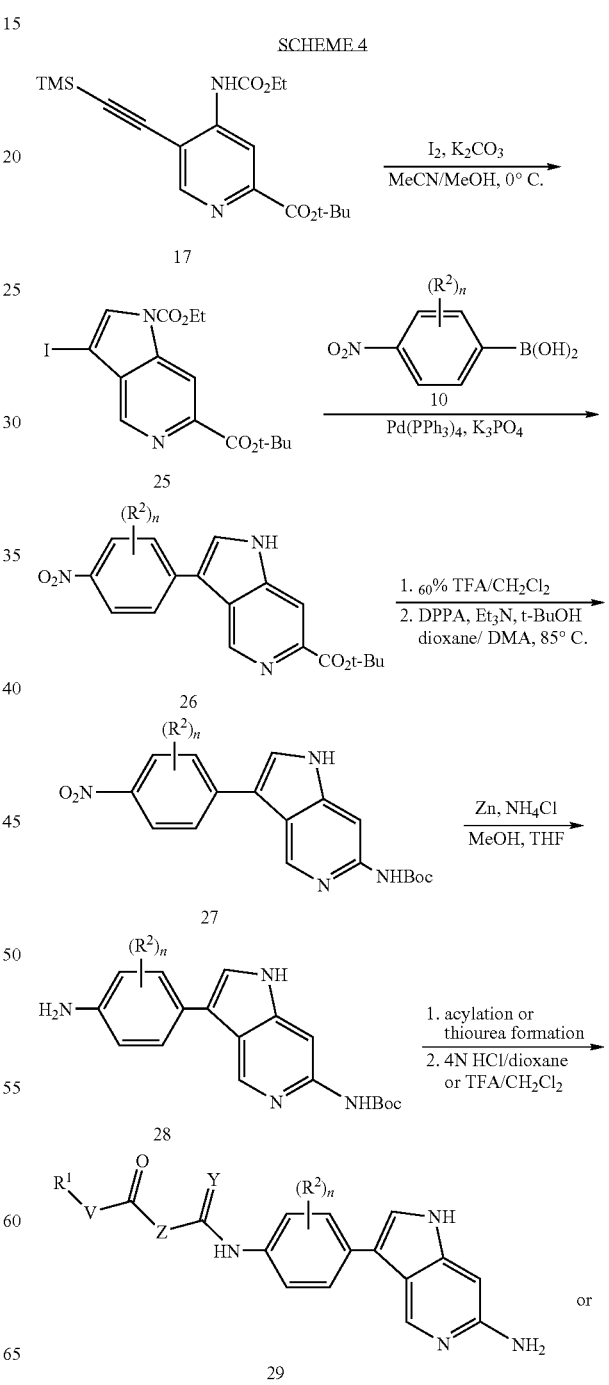

perature. Suzuki coupling of the intermediate 25 with a boronic acid 10 in the presence of a palladium catalyst and K₃PO₄ can provide compound 26. Acid promoted hydrolysis of compound 26 using trifluoroacetic acid in methylene chloride followed by Curtius rearrangement with diphenylphosphoryl azide (DPPA) in the presence of t-butanol can afford the N-Boc protected intermediate 27. Reduction of the nitro moiety of compound 27 with zinc dust and ammonium chloride in a THF-MeOH mixture can provide compound 28. Acylation or acylurea formation of intermediate 28 followed by removal of the N-Boc protecting group can be accomplished using chemistry previously described in Scheme 1 to generate the desired azaindole derivatives 29 and 30.

Regioisomeric azaindole derivatives 29 and 30 can be prepared using the synthetic route outlined in Scheme 4. The silylacetylene intermediate 17, which can be prepared using the chemistry illustrated in Scheme 3, can be converted to 6-tert-butyl-1-ethyl 3-iodo-1H-pyrrolo[3,2-c]pyridine-1,6-dicarboxylate (25) using iodine and a base, such as potassium carbonate in an acetonitrile-methanol mixture at low tem- -continued

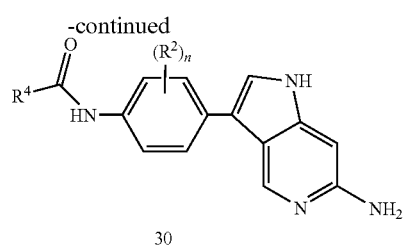

30

The compounds of Formulas I and II are useful in the treatment of a variety of cancers, including, but not limited to, the following:
 a) carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma;
 b) hematopoietic tumors of lymphoid lineage, including leukemia, acute lymphocytic leukemia, acute lymphoblastic leukemia, B-cell lymphoma, T-cell lymphoma, Hodgkin's lymphoma, non-Hodgkins lymphoma, hairy cell lymphoma and Burkett's lymphoma;
 c) hematopoietic tumors of myeloid lineage, including acute and chronic myelogenous leukemias, myelodysplastic syndrome and promyelocytic leukemia;
 d) tumors of mesenchymal origin, including fibrosarcoma and rhabdomyosarcoma;
 e) tumors of the central and peripheral nervous system, including astrocytoma, neuroblastoma, glioma and schwannomas; and
 f) other tumors, including melanoma, seminoma, teratocarcinoma, osteosarcoma, xenoderma pigmentosum, keratoctanthoma, thyroid follicular cancer and Kaposi's sarcoma.

Due to the key role protein kinases in the regulation of cellular proliferation in general, inhibitors could act as reversible cytostatic agents which may be useful in the treatment of any disease process which features abnormal cellular proliferation, e.g., benign prostatic hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections.

Compounds of Formulas I and II may be useful in the treatment of cancer (including but not limited to those types mentioned herein above), viral infections (including but not limited to herpevirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

Compounds of Formulas I and II may modulate the level of cellular RNA and DNA synthesis. These agents would therefore be useful in the treatment of viral infections (including but not limited to HIV, human papilloma virus, herpesvirus, poxvirus, Epstein-Barr virus, Sindbis virus and adenovirus).

Compounds of Formulas I and II may be useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse.

Compounds of Formulas I and II may also be useful in inhibiting tumor angiogenesis and metastasis.

The compounds of this invention may also be useful in combination (administered together or sequentially) with known anti-cancer treatments or anticancer agents as defined herein.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropyl-methylcellulose or hydroxypropyl-cellulose, or a time delay material such as ethyl cellulose, cellulose acetate buryrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS.TM. model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formulas I and II may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula I are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a compound according to this invention is administered into a human subject, the daily dosage will normally be determined by the prescribing physician with the dosage generally varying according to the age, weight, sex and response of the individual patient, as well as the severity of the patient's symptoms.

If formulated as a fixed dose, such combination products employ the compounds of this invention within the dosage range described above and the other pharmaceutically active agent or treatment within its approved dosage range. Compounds of Formulas I and II may also be administered sequentially with known anticancer or cytotoxic agents when a combination formulation is inappropriate. The invention is not limited in the sequence of administration; compounds of Formula I may be administered either prior to or after administration of the known anticancer or cytotoxic agent(s).

Assays

The pharmacological properties of the compounds of this invention may be confirmed by a number of pharmacological assays. The exemplified pharmacological assays which follow have been carried out using compounds according to the present invention.

| MET KINASE ASSAY | |
|---|---|
| Reagents | Substrate Mix Final Concentration |
| Stock Solution | |
| Tris-HCl, (1M, pH 7.4) | 20 mM |
| MnCl$_2$ (1M) | 1 mM |
| DTT(1M) | 1 mM |
| BSA (100 mg/ml) | 0.1 mg/ml |
| polyGlu$_4$/tyr (10 mg/ml) | 0.1 mg/mL |
| ATP(1 mM) | 1 µM |
| γ-ATP (10 µCi/µl) | 0.2 µCi/ml |
| Buffer | Enzyme mix |
| 20 ul 1M DTT | 4 ul GST/Met enzyme(3.2 mg/ml) = 10 ng/rxn |
| 200 ul 1M Tris-HCL, pH 7.4 | qs 12 ml Buffer |
| 20 ul 100 mg/ml BSA | |
| qs 20 ml H$_2$O | |

Incubation mixtures employed for the Met kinase assay contain the synthetic substrate polyGlu:Tyr, (4:1), ATP, ATP-γ-$^{33}$P and buffer containing Mn$^{++}$ and/or Mg$^{++}$, DTT, BSA, and Tris buffer. Reactions are incubated for 60 minutes at 27° C. and stopped by the addition of cold trichloroacetic acid (TCA) to a final concentration 4%. TCA precipitates are collected onto GF/C unifilter plates (Packard Instrument Co., Meriden, Conn.) using a Filtermate universal harvester (Packard Instrument Co., Meriden, Conn.) and the filters are quantitated using a TopCount 96-10 well liquid scintillation counter (Packard Instrument Co., Meriden, Conn.). Dose response curves are generated to determine the concentration required to inhibit 50% of kinase activity (IC$_{50}$). Compounds are dissolved at 10 mM in dimethyl sulfoxide (DMSO) and evaluated at six concentrations, each in quadruplicate. The final concentration of DMSO in the assay is 1%. IC$_{50}$ values are derived by non-linear regression analysis and have a coefficient of variance (SD/mean, n=6)=16%.

Preferred compounds of the present invention inhibit Met and KDR kinases with IC$_{50}$ values between 0.01 and 100 µM. More preferred compounds have IC$_{50}$ values of less than 1.0 µM, and more preferably, less than about 0.5 µM.

Further subject matter of the present invention includes pharmaceuticals for use as described above for treating cancer containing at least one compound of Formula I or II as defined above or pharmacologically acceptable acid addition salts thereof. Further, the use of a compound having Formula I or II as defined above for the preparation of a pharmaceutical having activity against proliferative diseases, such as cancer, is contemplated by the present invention.

The following examples and preparations describe the manner and process of making and using the invention and are illustrative rather than limiting. It should be understood that there may be other embodiments which fall within the spirit and scope of the invention as defined by the claims appended hereto.

EXAMPLES

The invention will now be further described by the following working examples. All reactions were carried out with continuous magnetic stirring under an atmosphere of dry nitrogen or argon. All evaporations and concentrations were carried out on a rotary evaporator under reduced pressure. Commercial reagents were used as received without additional purification. Solvents were commercial anhydrous grades and were used without further drying or purification. Flash chromatography was performed using silica gel (EMerck Kieselgel 60, 0.040-0.060 mm).

Analytical Reverse Phase (RP) HPLC was performed using a Phenomenex Luna C18 S5 4.6 mm×50 mm column or a YMC S5 ODS 4.6×50 mm column. In each case a 4 min linear gradient (from 100% A: %0 B to 0% A: 100% B) was used with the following mobile phase system: A=90% H$_2$O/MeOH+0.2% H$_3$PO$_4$; B=90% MeOH/H$_2$O+0.2% H$_3$PO$_4$ at flow rate=4 mL/min and detection at 220 nm.

Preparative Reverse Phase (RP) HPLC was performed with a linear gradient elution using H$_2$O/MeOH mixtures buffered with 0.1% trifluoroacetic acid and detection at 220 nm on one of the following columns: Shimadzu S5 ODS-VP 20×100 mm (flow rate=9 mL/min), or YMC S10 ODS 50×500 mm (flow rate=50 mL/min), or YMC S10 ODS 30×500 mm (flow rate=20 mL/min).

All final products were characterized by $^1$H NMR, RP HPLC, electrospray ionization (ESI MS) or atmospheric pressure ionization (API MS) mass spectrometry. $^1$H NMR spectra were obtained on either a 500 MHz JEOL or a 400 MHz Bruker instrument. $^{13}$C NMR spectra were recorded at 100 or 125 MHz. Field strengths are expressed in units of δ (parts per million, ppm) relative to the solvent peaks, and peak multiplicities are designated as follows: s, singlet; d, doublet; dd, doublet of doublets; dm, doublet of multiplets; t, triplet; q, quartet; br s, broad singlet; m, multiplet.

The following abbreviations are used for commonly used reagents: Boc or BOC: t-butyl carbamate; Fmoc: 9H-fluorenylmethyl carbamate; NMM: N-methylmorpholine; Ms: methanesulfonyl; DIEA or DIPEA: diisopropylethylamine or Hunig's base; NMP: N-methylpyrrolidinone; BOP reagent: benzotriazol-1-yloxytris(trimethylamino)phosphonium hexafluorophosphate; DCC: 1,3-dicyclohexylcarbodiimide; EDCI: 1-(dimethylaminopropyl)-3-ethylcarbodiimide hydrochloride; RT: room temperature; tR: retention time; h: hour(s); min: minute(s); PyBrOP: bromotripyrrolidinophosphonium hexafluorophosphate; TBTU: O-(1H-benzotriazol-1-yl)-N,N,N',N'-tetramethyluronium tetrafluoroborate; DMAP: 4-N,N-dimethylaminopyridine; HOBt: hydroxybenzotriazole; Na(OAc)$_3$BH: sodium triacetoxyborohydride; HOAc: acetic acid; TFA: trifluoroacetic acid; LiHMDS: lithium bis(trimethylsilyl)amide; DMSO: dimethyl sulfoxide; MeCN: acetonitrile; MeOH: methanol; EtOAc: ethyl acetate; DMF: dimethyl formamide; THF: tetrahydrofuran; DCE: 1,2-dichloroethane; Et$_2$O: diethyl ether.

Example 1

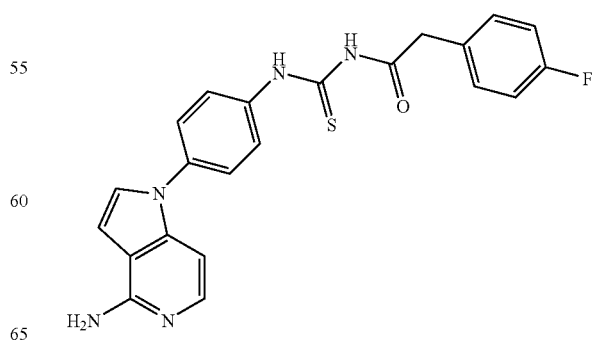

1-(4-(4-Amino-1H-pyrrolo[3,2-c]pyridin-1-yl)phenyl)-3-(2-(4-fluorophenyl)acetyl)thiourea, hydrochloride salt

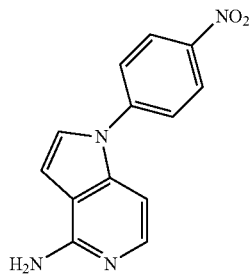

A) 1-(4-Nitrophenyl)-1H-pyrrolo[3,2-c]pyridin-4-amine

The title compound was prepared using the procedure described generally by Girgis, N. S. et al. (*J. Heterocyclic Chem.* 1989, 26, 317-325), the disclosure of which his incorporated by reference in its entirety, starting from 4-chloro-1H-pyrrolo[2,3-b]pyridine (see, generally, Cheng, C.-C. et al. *J. Physical Chem.* 2003, 107, 1459-1471, incorporated by reference in its entirety.)

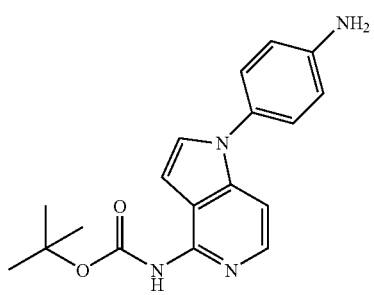

B) tert-Butyl 1-(4-aminophenyl)-1H-pyrrolo[3,2-c]pyridin-4-ylcarbamate

A solution of 1-(4-nitrophenyl)-1H-pyrrolo[3,2-c]pyridin-4-amine (37 mg, 0.15 mmol) in t-butanol (1 mL) was treated with di-tert-butyl dicarbonate (Aldrich, 35 mg, 0.16 mmol). The reaction mixture was stirred at 45° C. for 24 h and concentrated in vacuo. The residue was immediately dissolved in a THF-MeOH solution (3:2, 1 mL) and treated sequentially with Zn powder (95 mg, 1.5 mmol) and ammonium chloride (79 mg, 1.5 mmol). The reaction mixture was stirred at ambient temperature for 4 h, filtered, and the filtrate was concentrated in vacuo. The residue was then partitioned between EtOAc (5 mL) /H$_2$O (5 mL). The layers were separated and the aqueous phase was extracted with EtOAc (3×5 mL). The combined organics were washed with saturated aq. NaCl soln. (2×10 mL), dried (Na$_2$SO$_4$) and concentrated in vacuo. The crude product was purified using a Chromatotron (1 mm SiO$_2$ GF rotor, eluting with 5% MeOH-CHCl$_3$) to afford the title compound (27 mg, 57% over two steps) as an off-white solid. LCMS (ESI$^+$) m/z 325 (M+H)$^+$; HPLC t$_R$=2.44 min.

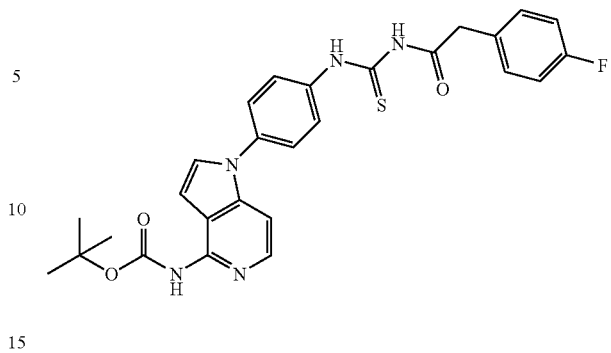

C) tert-Butyl 1-(4-(3-(2-(4-fluorophenyl)acetyl)thioureido)phenyl)-1H-pyrrolo[3,2-c]pyridin-4-ylcarbamate 4-Fluorophenylacetyl chloride (13 µL, 16 mg, 0.093 mmol) was added to a suspension of NaSCN (8.1 mg, 0.10 mmol) in EtOAc (1 mL) and the resulting mixture stirred at RT for 30 min. This mixture was then added to a solution of tert-butyl 1-(4-aminophenyl)-1H-pyrrolo[3,2-c]pyridin-4-ylcarbamate (25 mg, 0.077 mmol) in CH$_2$Cl$_2$ (0.5 ml) and the resulting mixture stirred at ambient temperature for 2 h. The mixture was concentrated in vacuo and the residue partitioned between EtOAc/H$_2$O (1:1, 5 mL). The EtOAc phase was separated, washed with brine, dried (MgSO$_4$) and concentrated in vacuo. The crude product was purified using a Chromatotron (1 mm SiO$_2$ GF rotor, 2-5% MeOH—CHCl$_3$ gradient elution) to give the title compound (10 mg, 25%) as a yellow solid. LCMS (ESI$^+$) m/z 520 (M+H)$^+$; HPLC t$_R$=3.81 min.

D) 1-(4-(4-Amino-1H-pyrrolo[3,2-c]pyridin-1-yl)phenyl)-3-(2-(4-fluorophenyl)acetyl)thiourea, hydrochloride salt tert-Butyl 1-(4-(3-(2-(4-fluorophenyl)acetyl)thioureido)phenyl)-1H-pyrrolo[3,2-c]pyridin4-ylcarbamate (10 mg, 0.19 mmol) was treated with 4 N HCl in dioxane (2 mL) and stirred at RT for 2 h. The reaction mixture was concentrated in vacuo and the remaining solid was triturated twice with EtOAc (~0.5 mL) to afford the title compound as the hydrochloride salt (6.5 mg, 74%). $^1$H NMR (DMSO-d$_6$) δ 12.48 (s, 1H), 11.80 (s, 1H), 8.42 (br s, 2H), 7.88 (d, 2H, J=8.5 Hz), 7.78 (d, 1H, J=3.1 Hz), 7.64-7.55 (m, 3H), 7.38 (dd, 2H, J=7.6, 6.2 Hz), 7.27 (d, 1H, J=3.1 Hz), 7.18 (t, 2H, J=9.7 Hz), 6.97 (d, 1H, J=7.0 Hz), 3.83 (s, 2H); LCMS (ESI$^+$) m/z 420 (M+H)$^+$; HPLC t$_R$=3.42 min.

Example 2

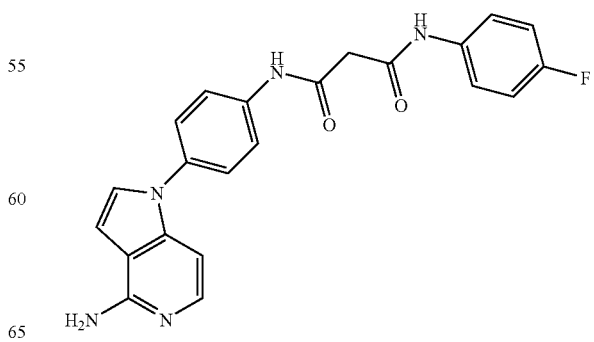

1-(4-(4-Amino-1H-pyrrolo[3,2-c]pyridin-1-yl)phenyl)-3-(2-(4-fluorophenyl)acetyl)thiourea, hydrochloride salt

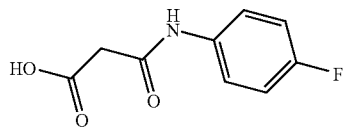

A) 3-(4-Fluorophenylamino)-3-oxopropanoic acid

To a solution of ethyl 3-chloro-3-oxopropanoate (5.0 mL, 40 mmol, Aldrich) in methylene chloride (100 mL) at 0° C. was added diisopropylethylamine (8.4 mL, 48 mmol) followed by 4-fluoroaniline (3.6 mL, 38 mmol, Aldrich). The reaction mixture was stirred at room temperature overnight and was then quenched with 100 mL of saturated NaHCO₃ solution. The aqueous layer was extracted with chloroform (3×100 mL). The combined organic extracts were dried over anhydrous Na₂SO₄ and concentrated in vacuo to give the crude product as a yellow oil that solidified upon standing (10 g). ¹H NMR (CDCl₃) δ 9.30 (br s, 1H), 7.55 (m, 2H), 7.05 (t, 2H, J=8.8 Hz), 4.28 (q, 2H, J=7.2 Hz), 3.49 (s, 2H), 1.35 (t, 3H, J=7.1 Hz); MS(ESI⁺) m/z 226.11 (M+H)⁺.

The above ester was dissolved in 100 mL of ethanol and cooled to 0° C. 1 N aq. NaOH solution (100 mL) was added and the reaction was stirred at 0° C. for 1 h. The reaction was concentrated in vacuo to remove ethanol. The aqueous solution was extracted with EtOAc (50 mL) and was then made acidic with 1 N aq HCl solution. The aqueous solution was extracted with EtOAc (5×100 mL). The combined organic extracts were dried over anhydrous Na₂SO₄ and concentrated in vacuo to give the crude product as a yellow solid (6.31 g, 84%) which was used without further purification. ¹H NMR (DMSO-d₆) δ 12.9 (br s, 1H), 10.3 (br s, 1H), 7.59 (m, 2H), 7.16 (t, 2H, J=8.9 Hz), 3.34 (s, 2H); MS(ESI⁺) m/z 198.43 (M+H)⁺.

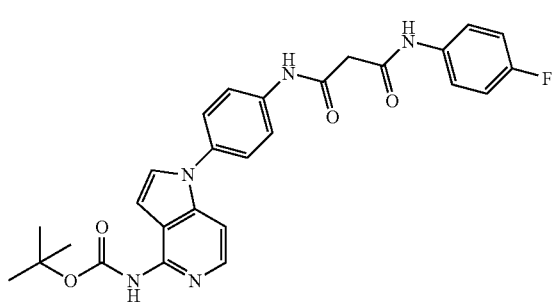

B) tert-Butyl 1-(4-(3-(4-fluorophenylamino)-3-oxopropanamido)phenyl)-1H-pyrrolo[3,2-c]pyridin-4-ylcarbamate A solution of tert-butyl 1-(4-aminophenyl)-1H-pyrrolo[3,2-c]pyridin-4-ylcarbamate (27 mg, 0.083 mmol, Compound B of Example 1) in DMF (1 mL) was treated with 3-(4-fluorophenylamino)-3-oxopropanoic acid (25 mg, 0.13 nmol), DIPEA (21 μL, 0.13 mmol) and TBTU (40 mg, 0.13 mmol) and the mixture stirred at RT for 16 h. The mixture was concentrated in vacuo to remove the DMF and the residue was partitioned between EtOAc (2 mL) and saturated sodium bicarbonate solution (2 mL). The EtOAc phase was washed with 10% aqueous LiCl (2 mL), brine (2 mL), dried (MgSO₄) and concentrated in vacuo. The crude product was purified using a Chromatotron (1 mm SiO₂ GF rotor, 2-5% MeOH-CHCl₃ gradient elution) to give the title compound (37 mg, 88%) as an off-white solid. LCMS (ESI⁺) m/z 504 (M+H)⁺; HPLC t_R=3.49 min.

C) N¹-(4-(4-amino-1H-pyrrolo[3,2-c]pyridin-1-yl)phenyl)-N³-(4-fluorophenyl)malonamide tert-Butyl 1-(4-(3-(4-fluorophenylamino)-3-oxopropanamido)phenyl)-1H-pyrrolo[3,2-c]pyridin-4-ylcarbamate (37 mg, 0.074 mmol) was treated with 4 N HCl in dioxane (2 mL) and stirred at RT for 2 h. The reaction mixture was concentrated in vacuo and the residue was partitioned between saturated NaHCO₃ (2 mL) and EtOAc (2 mL). The EtOAc phase was separated, dried (MgSO₄) and concentrated in vacuo. The residue was purified by flash chromatography (SiO₂, 10-15% MeOH-CHCl₃ gradient elution) to afford the title compound (7.0 mg, 23%) as a white solid. ¹H NMR (DMSO-d₆) δ 10.58 (s, 1H), 10.38 (s, 1H), 8.01 (br s, 2H), 7.84 (d, 2H, J=9.0 Hz), 7.69-7.62 (m, 3H), 7.60 (d, 1H, J=7.4 Hz), 7.52 (d, 2H, J=9.0 Hz), 7.20-7.13 (m, 3H), 6.91 (d, 1H, J=8.2 Hz), 3.52 (s, 2H); LCMS (ESI⁺) m/z 404 (M+H)⁺; HPLC t_R=2.98 min.

Example 3

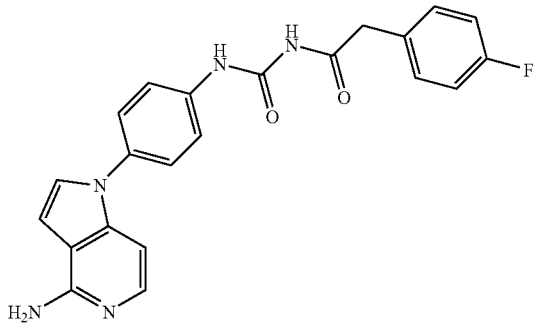

1-(4-(4-Amino-1H-pyrrolo[3,2-c]pyridin-1-yl)phenyl)-3-(2-(4-fluorophenyl)acetyl)urea, hydrochloride salt

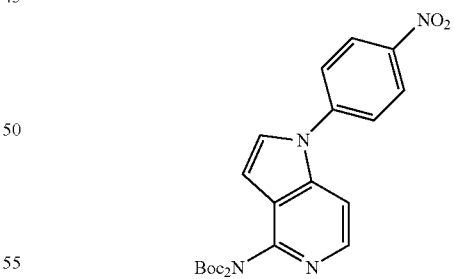

A) Bis-tert-butyl 1-(4-nitrophenyl)-1H-pyrrolo[3,2-c]pyridin-4-yl-dicarbamate

Sodium hydride (60%, 0.16 g, 3.9 mmol, 2.0 eq) was added to a solution of 1-(4-nitrophenyl)-1H-pyrrolo[3,2-c]pyridin-4-amine (Compound A of Example 1, 0.50 g, 2.0 mmol, 1.0 eq) in DMF (10 mL) at room temperature and the reaction mixture was stirred at room temperature for 2 h. Di-tert-butyldicarbonate (0.86 g, 4.0 mmol, 2.0 eq) was added to the solution and the reaction mixture was stirred for 12 h. The reaction mixture was quenched with aq. LiCl (10%) and the solution was extracted with EtOAc (3×70 mL). The combined organic layers were wash with aq. LiCl (10%), dried (Na₂SO₄), filtered and concentrated in vacuo. The residue was purified by flash chromatography (SiO₂, eluting 2/1 hexane/EtOAc) to afford the title compound (0.105 g, 15%) as a solid. ¹H NMR (CDCl₃) δ 8.48 (m, 2H), 8.34 (m, 1H), 7.71 (m, 2H), 7.46-7.50 (m, 2H), 6.77 (m, 1H), 1.50 (s, 18H); MS(ESI⁺) m/z 455 (M+H)⁺.

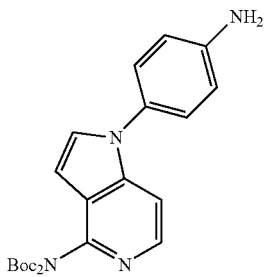

B) Bis-tert-butyl 1-(4-aminophenyl)-1H-pyrrolo[3,2-c]pyridin-4-yl-dicarbamate

A suspension of bis-tert-butyl 1-(4-nitrophenyl)-1H-pyrrolo[3,2-c]pyridin-4-yl-dicarbamate (0.04 g, 0.088 mmol, 1.0 eq) and PtO₂ (catalytic) in EtOH (5 mL) was stirred under a blanket of hydrogen (50 psi) at room temperature for 1 h. The reaction mixture was filtered through a bed of Celite and the filtrate was concentrated in vauo to afford the title compound (0.037 g, 100%) as a solid. ¹H NMR (CDCl₃) δ 8.12 (br m, 1H), 7.15-7.22 (m, 6H), 6.73-6.75 (m, 2H), 6.52 (br m, 1H), 1.41 (s, 18H); MS(ESI⁺) m/z 425 (M+H)⁺, calc: 425.2189, found: 425.2177.

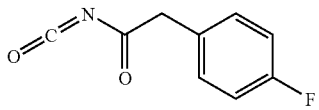

C) 2-(4-Fluorophenyl)acetyl isocyanate

Silver cyanate (0.912 g, 6.08 mmol, 1.05 eq) was added to a solution of 4-fluorophenylacetyl chloride (0.794 ml, 5.79 mmol, 1.0 eq, Lancaster) in toluene (20 mL) at room temperature. The reaction mixtures was shielded from light and heated to reflux. After 60 minutes the mixture was cooled to room temperature and filtered (Acrodisc, PTFE 0.2 μM) to give a 0.29 M solution of 2-(4-fluorophenyl)acetyl isocyanate in toluene, which was used without further purification.

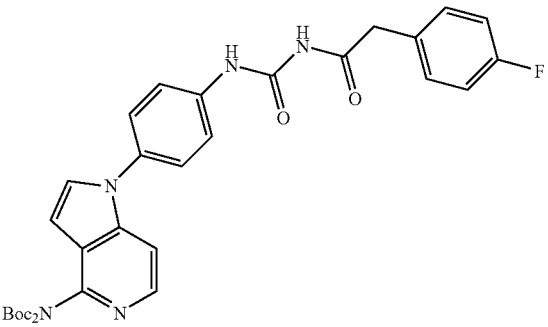

D) Bis-tert-butyl 1-(4-(3-(2-(4-fluorophenyl)acetyl)ureido)phenyl)-1H-pyrrolo[3,2-c]pyridin-4-yl-dicarbamate A solution of 2-(4-fluorophenyl)acetyl isocyanate (0.29 M, in toluene, 0.190 mL, 0.055 mmol, 1.3 eq) was added to a solution of bis-tert-butyl 1-(4-aminophenyl)-1H-pyrrolo[3,2-c]pyridin-4-yl-dicarbamate (0.18 g, 0.0425 mmol, 1.0 eq) in methylene chloride (0.50 mL) at room temperature. The reaction mixture was stirred at room temperature for 8 h at which point it was then concentrated in vacuo. The residue was purified by flash chromatography (SiO₂, eluting 2/1 to 1/2 hexane/EtOAc) to afford the title compound (0.018g, 72%) as a solid. ¹H NMR (CDCl₃) δ 8.15-8.20 (m, 1H), 7.61-7.64 (m, 2H), 7.36-7.38 (m, 2H), 7.24-7.28 (m, 6H), 7.00-7.04 (m, 2H), 6.57-6.58 (m, 1H), 3.69 (s, 2H), 1.37 (s, 18H); MS(ESI⁺) m/z 604 (M+H)⁺, calc: 604.2571, found: 604.2520

E) 1-(4-(4-Amino-1H-pyrrolo[3,2-c]pyridin-1-yl)phenyl)-3-(2-(4-fluorophenyl)acetyl)urea, hydrochloride salt A solution of bis-tert-butyl 1-(4-(3-(2-(4-fluorophenyl)acetyl)ureido)phenyl)-1H-pyrrolo[3,2-c]pyridin-4-yl-dicarbamate (0.018 g, 0.030 mmol, 1.0 eq) in anhydrous HCl in dioxane (4 N, 1.0 mL, 4.0 mmol, 133 eq) was stirred at 0° C. for 15 minutes. The reaction mixture was warmed to room temperature and stirred for an additional 30 minutes. The reaction mixture was then concentrated in vacuo and the residue was triturated with Et₂O (3×1 mL). The filtrate was discarded and the solid was dried in vacuo to afford the title compound as a solid (0.008 g, 62%). ¹H NMR (CD₃OD) δ 10.85 (s, 1H), 7.78-7.80 (m, 2H), 7.61-7.62 (m, 1H), 7.50-7.54 (m, 3H), 7.37-7.40 (m, 2H), 7.08-7.16 (m, 4H), 7.01-7.02 (m, 1H), 3.75 (s, 2H); MS(ESI⁺) m/z 404 (M+H)⁺, calc: 404.1523, found: 404.1524.

Example 4

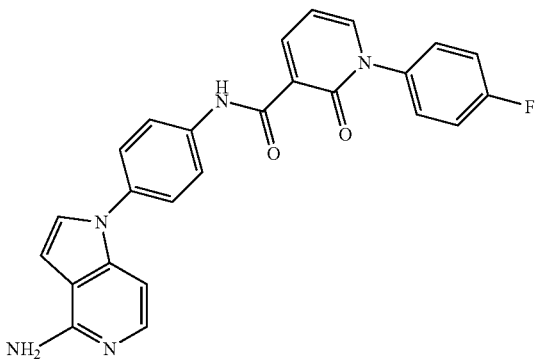

N-(4-(4-Amino-1H-pyrrolo[3,2-c]pyridin-1-yl)phenyl)-1-(4-fluorophenyl)-2-oxo-1,2-dihydropyridine-3-carboxamide, hydrochloride salt

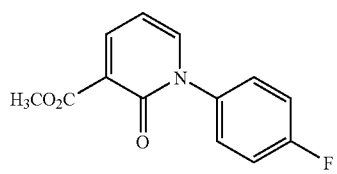

A) Methyl 1-(4-fluorophenyl)-2-oxo-1,2-dihydropyridine-3-carboxylate

To a solution of methyl 2-oxo-2H-pyran-3-carboxylate (Aldrich, 2.31 g, 15 mmol) in THF (40 mL) and DMF (10 mL) at rt was added a solid of 4-fluoroaniline (1.67 g, 15 mmol), and the reaction mixture was stirred for 2.5 h. Solid precipitation was observed. To the 4-fluoroaniline adduct intermediate formed via Michael addition was added in situ EDCI·HCl (3.85 g, 20 mmol) and DMAP (120 mg) at rt. The reaction mixture was stirred at rt overnight. To the reaction mixture were added 1 N aq. HCl (50 mL) and EtOAc (150 mL). The EtOAc layer was separated, and the aqueous layer was washed with EtOAc (150 mL). The combined EtOAc layers were dried over MgSO$_4$ and concentrated in vacuo to obtain a semi-solid material (~4.4 g). To this crude product were added ether (100 mL) and methanol (15 mL). The mixture was stirred, and the solid was filtered to obtain the undesired solid product (870 mg). The filtrate solution was concentrated in vacuo to obtain a semi-solid crude desired product (2.95 g, crude 80%) which was sufficiently pure to use in the subsequent step without further purification. $^1$H NMR (DMSO-d$_6$) δ 8.23 (dd, 1H, J=7.2, 2.2 Hz), 7.57 (dd, 1H, J=6.6, 1.7 Hz ), 7.32-7.34 (m, 2H), 7.17 (t, 2H, J=8.8 Hz), 6.32 (t, 1H, J=7.1 Hz), 3.89 (s, 3H); MS(ESI$^+$) m/z 248.2 (M+H)$^+$.

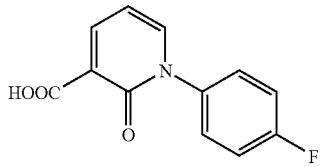

B) 1-(4-Fluorophenyl)-2-oxo-1,2-dihydropyridine-3-carboxylic acid

A mixture of methyl 1-(4-fluorophenyl)-2-oxo-1,2-dihydropyridine-3-carboxylate (crude 2.45 g, 12 mmol) and 6 N aq. NaOH (2.5 mL) in methanol (60 mL) was stirred at rt for 4 h. To the reaction mixture was added conc. HCl (1 mL) slowly with stirring at rt, and the precipitated solid was filtered, washed with a small amount water and dried to obtain the desired acid product (2.1 g, 1$^{st}$ crop) as a yellow solid. The filtrate solution was concentrated in vacuo, and the residue was mixed with water (50 mL), washed with EtOAc (2×130 mL) The organic layers were dried over MgSO$_4$, and concentrated in vacuo. The residue was triturated with a small amount of ether to obtain the 2$^{nd}$ crop of acid product (195 mg, total 2.30 g, 82%). $^1$H NMR (DMSO-d$_6$) δ 8.47 (dd, 1H, J=7.2, 2.2Hz), 8.19 (dd, 1H, J=6.6, 1.7Hz), 7.62-7.60 (m, 2H), 7.42 (t, 2H, J=8.8 Hz), 6.78 (t, 1H, J=7.1 Hz); MS(ESI$^+$) m/z 234.2 (M+H)$^+$.

C) N-(4-(4-Amino-1H-pyrrolo[3,2-c]pyridin-1-yl)phenyl)-1-(4-fluorophenyl)-2-oxo-1,2-dihydropyridine-3-carboxamide, hydrochloride salt Bis-tert-butyl 1-(4-aminophenyl)-1H-pyrrolo[3,2-c]pyridin-4-yl-dicarbamate (Compound B of Example 3, 0.18 g, 0.043 mmol, 1.0 eq) was added to a solution of 1-(4-fluorophenyl)-2-oxo-1,2-dihydropyridine-3-carboxylic acid (0.011 g, 0.047 mmol, 1.1 eq) and TBTU (0.018, 0.047 mmol, 1.1 eq) in DMF (0.50 mL) at room temperature. Diisopropylethylamine (0.008 mL, 0.047 mmol, 1.1 eq) was added to the reaction mixture and stirring was continued for 8 h. The reaction mixture was concentrated in vacuo and the residue was purified by reverse phase HPLC (YMC C-18 column, 30 min. gradient 25-90% aq. MeOH with 0.1% TFA). The appropriate fractions were concentrated in vacuo and the residue treated with anhydrous HCl (4 N in dioxane) at 0° C. The solution was concentrated in vacuo and the later procedure repeated three times. The residue was triturated with Et$_2$O, discarding the filtrate and the solid was dried in vacuo to afford the title compound (0.003 g, 17%) as a white solid. $^1$H NMR (CD$_3$OD) δ 7.85-7.87 (m, 2H), 7.56-7.63 (m, 3H), 7.24-7.46 (m, 6H), 7.03-7.09 (m, 3H), 6.94 (br m, 1H); MS(ESI$^+$) m/z 440 (M+H)$^+$, calc: 440.1523, found: 440.1517.

Example 5

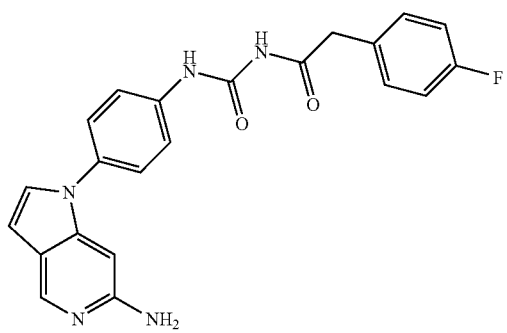

1-(4-(6-Amino-1H-pyrrolo[3,2-c]pyridin-1-yl)phenyl)-3-(2-(4-fluorophenyl)acetyl)urea, trifluoroacetic acid salt

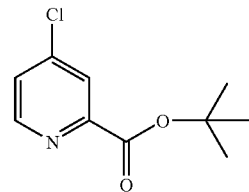

A) tert-Butyl 4-chloropicolinate

A mixture of picolinic acid (Aldrich, 10.5 g, 85.4 mmol), and sodium bromide (927 mg, 9.1 mmol) in thionyl chloride (40 mL) was refluxed for 24 h. Thionyl chloride was removed in vacuo, and the 4-chloropicolinyl chloride (12.6 g, 84%) was obtained by vacuum distillation to give a yellow solid.

To a solution of t-butanol (25 mL), pyridine (20 mL) and 1,2-dichloroethane (80 mL) at −40° C., was added a solution of 4-chloropicolinyl chloride (9.0 g, 51.1 mmol) in dichloroethane (60 mL). The mixture was heated at 50° C. for 24 h. The mixture was diluted with dichloromethane, washed with 5% citric acid, and sat. K$_2$HPO$_4$ aq. solution. The organic layer was dried over MgSO$_4$. The product was purified by flash column chromatography (SiO$_2$, eluting with 20% EtOAc/CH$_2$Cl$_2$) to give a clear oil (9.8 g, 90%). LC-MS: m/z 213 (M$^+$), 158 (M-Bu$^+$).

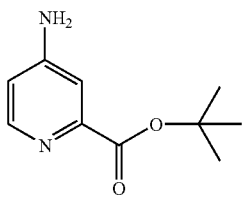

B) tert-Butyl 4-aminopicolinate

A mixture of tert-butyl 4-chloropicolinate (3.8 g, 17.8 mmol) and sodium azide (1.74 g, 26.8 mmol) in DMSO (20 mL) was heated at 130° C. for 15 h. The mixture was poured into water (80 mL), extracted three times with EtOAc. The combined organic solutions was dried over $MgSO_4$. The solid was filtered off, and the filtrate was concentrated in vacuo to give a residue which was heated with $PPh_3$ in $THF/H_2O$ (9:1, 40 mL) at 70° C. overnight. The mixture was diluted with EtOAc, washed with sat. $K_2HPO_4$ aq. solution. The organic layer was dried over $MgSO_4$ and the product was purified by flash column chromatography ($SiO_2$, 5% MeOH in EtOAc) to afford a white solid (1.8 g, 52%). LC-MS: m/z 195 $(M+H)^+$.

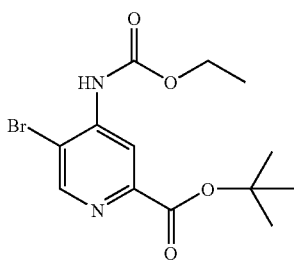

C) tert-Butyl 5-bromo-4-(ethoxycarbonyl)picolinate

To a solution of tert-butyl 4-aminopicolinate (1.97 g, 10 mmol) in 1,2-dichloroethane (60 mL) at 0° C., was added N-bromosuccinimide (1.78 g, 10 mmol) in small portions over a period of 1 h. The mixture was stirred at 0° C. for 1 h, diluted with $CH_2Cl_2$, washed with brine, and dried over $MgSO_4$. The brominated product was purified by flash column chromatography ($SiO_2$, 30% $EtOAc/CH_2Cl_2$) to give a yellow solid (2.2 g, 81%). LC-MS: m/z 273 $(M^+)$.

To a solution of tert-butyl 4-amino-5-bromopicolinate (546 mg, 2 mmol) in $CH_2Cl_2$ (5 mL) and pyridine (1 mL) at 0° C., was added ethyl chloroformate (271 mg, 2.5 mmol). The mixture was stirred at rt for 2 h, diluted with dichloromethane, washed with 5% citric acid, and sat. $K_2HPO_4$ aq. solution. The organic layer was dried over $MgSO_4$ and the product was purified by flash column chromatography ($SiO_2$, eluting with 20% $EtOAc/CH_2Cl_2$) to give a white solid (570 mg, 83%). LC-MS: m/z 345 $(M^+)$.

D) tert-Butyl 4-(ethoxycarbonyl)-5-(2-(trimethylsilyl)ethynyl)picolinate

A mixture of tert-butyl 5-bromo-4-(ethoxycarbonyl)picolinate (483 mg, 1.4 mmol), trimethylsilylacetylene (206 mg, 2.1 mmol), $Pd(PPh_3)_2Cl_2$ (99 mg, 0.14 mmol) and CuI (45 mg, 0.21 mmol) in triethylamine (3 mL) and THF (2 mL) in a sealed tube was passed through a stream of Ar for 5 min, and then heated at 105° C. for 1 h. The mixture was diluted with $THF/CH_2Cl_2$ (1:1), filtered through a pad of Celite®. The filtrate was concentrated in vacuo to give a residue, which was dissolved in $CH_2Cl_2$ (5 mL) and pyridine (0.5 mL) at 0° C. To this solution was added ethyl chloroformate (0.25 mL) and the resulting mixture was stirred at 0° C. for 30 min. The mixture was diluted with $CH_2Cl_2$, washed with sat. aq. $K_2HPO_4$ solution and dried over $MgSO_4$. The product was purified by flash column chromatography ($SiO_2$, 10% $EtOAc/CH_2Cl_2$) to afford a yellow solid (380 mg, 75%). LC-MS: m/z 363 $(M+H)^+$.

E) tert-Butyl 1H-pyrrolo[3,2-c]pyridine-6-carboxylate

A solution of tert-butyl 4-(ethoxycarbonyl)-5-(2-(trimethylsilyl)ethynyl) picolinate (340 mg, 0.94 mmol), tetrabutylammonium fluoride (1 M in THF, 3 mL) in THF (5 mL) was refluxed for 30 min. The solvent was removed in vacuo and the product was purified by flash column chromatography ($SiO_2$, 40% $EtOAc/CH_2Cl_2$) to give a yellow solid (152 mg, 74%). LC-MS: m/z 219 $(M+H)^+$.

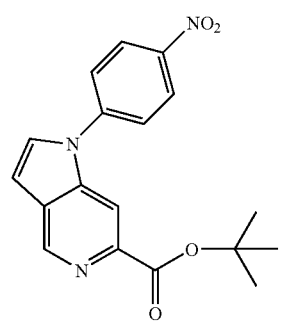

F) tert-Butyl 1-(4-nitrophenyl)-1H-pyrrolo[3,2-]pyridine-6-carboxylate

To a solution of tert-butyl 1H-pyrrolo[3,2-c]pyridine-6-carboxylate (120 mg, 0.55 mmol) in DMF (3 mL) at rt, was added NaH (60% in mineral oil, 26.4 mg, 0.66 mmol). The mixture was stirred for 10 min and 4-fluoronitrobenzene (155 mg, 1.1 mmol) was added to the reaction. The resulting mixture was stirred at rt for 1 h. The reaction was quenched with sat. aq. sodium citrate solution, extracted with EtOAc and dried over MgSO$_4$. The product was purified by flash column chromatography (SiO$_2$, 25% EtOAc/CH$_2$Cl$_2$) to give a yellow solid (137 mg, 73%).

LC-MS: m/z 340 (M+H)$^+$.

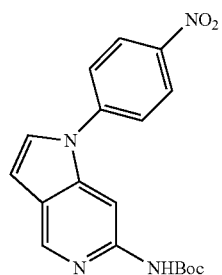

G) tert-Butyl 1-(4-nitrophenyl)-1H-pyrrolo[3,2-c]pyridin-6-ylcarbamate

A solution of tert-butyl 1-(4-nitrophenyl)-1H-pyrrolo[3,2-c]pyridine-6-carboxylate (150 mg, 0.44 mmol) in 50% TFA/CH$_2$Cl$_2$ (2 mL) was stirred at rt for 6 h. The solvent was removed in vacuo and the residue was treated with 5 mL of pH 7 buffer solution. The solid was collected by filtration, rinsed with water, dried in vacuo to give a white solid (carboxylic acid, 130 mg, 100%). LC-MS: m/z 284 (M+H)$^+$.

A mixture of the above carboxylic acid (125 mg, 0.44 mmol), DPPA (133 mg, 0.48 mmol), triethylamine (49 mg, 0.48 mmol) in THF (2 mL) and t-BuOH (3 mL) with 4 Å molecular sieves (0.5 g) in a sealed tube was heated at 85° C. for 24 h. The mixture was diluted with THF, filtered through a short pad of Celite®. The desired product was purified by prep-HPLC to afford a yellow solid (35 mg, 22% yield). LC-MS: m/z 355 (M+H)$^+$.

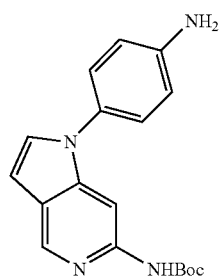

H) tert-Butyl 1-(4-aminophenyl)-1H-pyrrolo[3,2-c]pyridin-6-ylcarbamate

A mixture of tert-butyl 1-(4-nitrophenyl)-1H-pyrrolo[3,2-c]pyridin-6-ylcarbamate (35 mg, 0.10 mmol), zinc powder (80 mg), and NH$_4$Cl (100 mg) in MeOH (3 mL) and THF (2 mL) was stirred at rt for 15 h. The mixture was diluted with EtOAc, filtered through a pad of Celite®. The filtrate was washed with brine, dried over MgSO$_4$ and concentration in vacuo to afford the title compound as a solid (29 mg, 89%) was obtained. LC-MS: m/z 325 (M+H)$^+$.

I) 1-(4-(6-Amino-1H-pyrrolo[3,2-c]pyridin-1-yl)phenyl)-3-(2-(4-fluorophenyl)acetyl)urea, trifluoroacetic acid salt To a solution of tert-butyl 1-(4-aminophenyl)-1H-pyrrolo[3,2-c]pyridin-6-ylcarbamate (7 mg, 0.02 mmol) in THF (0.8 mL) at rt, was added 2-(4-fluorophenyl)acetyl isocyanate (Compound C of Example 3, 0.033 mmol). The resulting mixture was stirred at rt for 1 h and reaction was concentrated in vacuo. The residue was purified by prep HPLC to give a white solid (8 mg, 72%). LC-MS: m/z 504 (M+H)$^+$. The solid was treated with 2 mL of 60% TFA/CH$_2$Cl$_2$ for 1 h at rt and the reaction mixture was concentrated in vacuo to afford the title compound (8 mg) as a TFA salt (white solid). $^1$H NMR (CD$_3$OD) δ 8.29 (s, 1H), 7.67 (dd, 2H, J=8.8, 2.0 Hz), 7.49 (d, 1H, J=4.0 Hz), 7.41 (2H, J=8.8, 2.0 Hz), 7.28 (m, 2H), 7.00 (m, 2H), 6.73 (m, 2H), 3.63 (s,2H); LC-MS: m/z 404 (M+H)$^+$.

Example 6

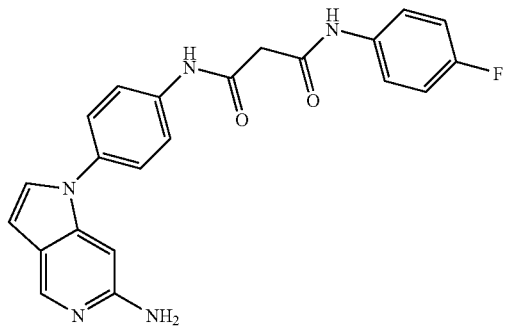

N1-(4-(6-amino-1H-pyrrolo[3,2-c]pyridin-1-yl)phenyl)-N3-(4-fluorophenyl)malonamide, trifluoroacetic acid salt To a mixture of tert-butyl 1-(4-aminophenyl)-1H-pyrrolo[3,2-c]pyridin-6-ylcarbamate (Compound H of Example 5, 7 mg, 0.02mmol), 3-(4-fluorophenylamino)-3-oxopropanoic acid (Compound A of Example 2, 8.5 mg, 0.044 mmol) in DMF at rt, was added HATU (17 mg, 0.044 mmol), and followed by diisopropylethylamine (0.05 mL). The resulting mixture was stirred for 1 h, concentrated in vacuo and the resulting residue was purified by prep-HPLC to afford a white solid (10 mg, 90% yield). LC-MS: m/z 504 (M+H )$^+$. This Boc derivative (7 mg) was treated with 2 mL of 60% TFA/CH$_2$Cl$_2$ for 1 h at rt and the reaction mixture was concentrated in vacuo to give the title compound as a TFA salt (7 mg, white solid). $^1$H NMR (CD$_3$OD) δ 8.29 (s, 1H), 7.78 (dd, 2H, J=8.0, 1.6 Hz), 7.52 (m, 3H), 7.43 (dd, 2H, J=8.0, 1.6 Hz), 6.99 (m, 2H), 7.00 (m, 2H), 6.74 (m, 2H), 3.49 (s,2H); LC-MS: m/z 404 (M+H)+.

Example 7

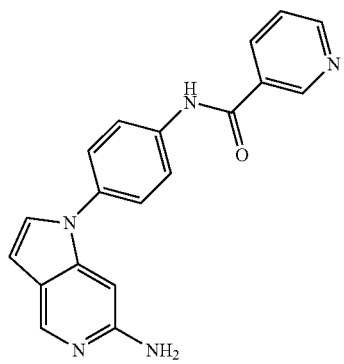

N-(4-(6-amino-1H-pyrrolo[3,2-c]pyridin-1-yl)phenyl)nicotinamide, trifluoroacetic acid salt To a mixture of tert-butyl 1-(4-aminophenyl)-1H-pyrrolo[3,2-c]pyridin-6-ylcarbamate (5 mg, 0.02 mmol) and nicotinyl chloride (HCl salt, 5.3 mg, 0.3 mmol) in THF (0.5 mL) at 0° C. under $N_2$, was added pyridine (0.05 mL). The resulting mixture was stirred at rt for 1 h and the solvent was removed in vacuo. The desired product was purified by prep. HPLC to afford a white solid (6 mg, 93% yield). LC-MS: m/z 430 (M+H)+. This Boc derivative (6 mg) was treated with 2 ML of 60% $TFA/CH_2Cl_2$ for 1 h at rt and the reaction mixture was concentrated in vacuo to give the title compound as a TFA salt (6.5 mg, white solid). $^1$H NMR ($CD_3OD$) δ 9.04 (s, 1H), 8.67 (d, 1H, J=4.4 Hz), 8.33 (m, 1H), 7.91 (dd, 2H, J=6.8 Hz, J=2.0 Hz), 7.45-7.60 (m, 4H), 6.78 (s, 1H), 6.75 (d, 1H, J =3.6 Hz), 3.49 (s,2H); LC-MS: m/z 330 (M+H)+.

Example 8

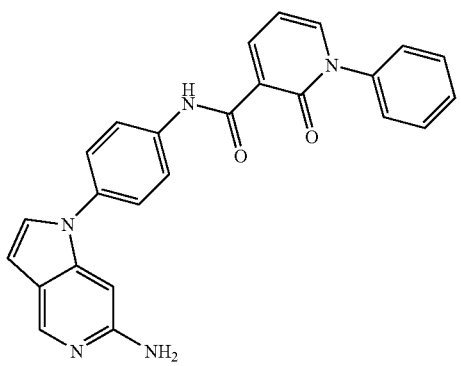

N-(4-(6-Amino-1H-pyrrolo[3,2-c]pyridin-1-yl)phenyl)-2-oxo-1-phenyl-1,2-dihydropyridine-3-carboxamide

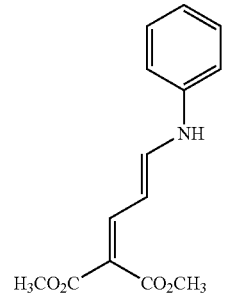

A) (E)-Dimethyl 2-(3-(phenylamino)allylidene)malonate

To a solution of 2-(3-methoxyallylidene)malonic acid dimethyl ester (Acros Organics, 200 mg, 1.0 mmol) in THF (2 mL) at rt was added aniline (300 mg, 3.2 mmol) and the reaction mixture was heated at 60° C. for 8.5 h. Purification of the reaction mixture by preparative HPLC afforded the desired product (150 mg, 57%) as a yellow solid. $^1$H NMR (DMSO-$d_6$) δ 10.16 (d, 1H, J=12.7Hz), 8.06 (t, 1H, J=12.7 Hz), 7.74 (d, 1H, J=12.7 Hz), 7.30 (t, 2H, J=8.7 Hz), 7.16 (d, 2H, J=7.7 Hz), 6.98 (t, 1H, J=7.7 Hz), 6.35 (t, 1H, J=12.1 Hz), 3.69 (s, 3H), 3.65 (s, 3H).

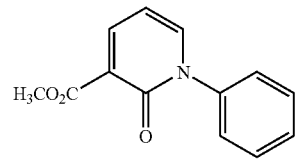

B) Methyl 2-oxo-1-phenyl-1,2-dihydropyridine-3-carboxylate

To a solution of (E)-dimethyl 2-(3-(phenylamino)allylidene)malonate (130 mg, 0.50 mrnol) in methanol (8 mL) at rt was added NaH (50 mg of the 60% NaH in oil, 1.2 mmol) and the mixture was stirred at rt for 3 h. Acetic acid (0.3 mL) was added to the mixture, concentrated to a volume of 4 mL, and purificationof the reaction mixture by preparative HPLC provided the desired product (105 mg, 92%) as a yellow solid. $^1$H NMR ($CD_3OD$) δ 8.30 (dd, 1H, J=7.2, 2.2 Hz), 7.87 (dd, 1H, J=6.6, 1.7 ), 7.57-7.38 (m, 5H), 6.53 (t, 1H, J=7.0 Hz), 3.84 (s, 3H); MS(ESI+) m/z 230.3 (M+H)+.

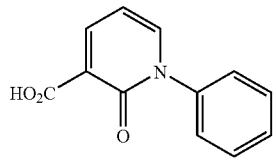

C) 2-Oxo-1-phenyl-1,2-dihydropyridine-3-carboxylic acid

A mixture of methyl 2-oxo-1-phenyl-1,2-dihydropyridine-3-carboxylate (70 mg, 0.31 mmol) and LiOH (40 mg) in methanol (6 mL) and water (1 mL) was stirred at rt overnight. To the reaction mixture were added EtOAc (50 mL) and 1 N aq HCl (15 mL), EtOAc layer was separated, dried over $MgSO_4$, and concentrated in vacuo to obtain the acid (55 mg, 83%) as a light yellow solid. $^1$H NMR (DMF-$d_7$) δ 11.77 (br s, 1H), 8.57 (dd, 1H, J=7.4, 2.0 Hz), 8.26 (dd, 1H, J=6.6, 1.6 Hz), 7.64-7.55 (m, 5H), 6.88 (t, 1H, J=7.0 Hz); MS(ESI+) m/z 216.2 (M+H)+.

D) N-(4-(6-amino-1H-pyrrolo[3,2-c]pyridin-1-yl)phenyl)-2-oxo-1-phenyl-1,2-dihydropyridine-3-carboxamide The title compound was obtained as a tan solid from tert-butyl 1-(4-aminophenyl)-1H-pyrrolo[3,2-c]pyridin-6-ylcarbamate (Compound H of Example 5) and 2-oxo-1-phenyl-1,2-dihydropyridine-3-carboxylic acid using a procedure similar to that for Example 4. ¹H NMR (DMSO-d₆) δ 8.54 (dd, 1H, J=7.2, 2.0 Hz), 8.48 (s, 1H), 8.09 (dd, 1H, J=6.4, 2.4 Hz), 7.89 (d, 2H, J=8.8 Hz), 7.71 (d, 1H, J=3.6 Hz), 7.4-8.55 (m, 7H), 6.92 (s, 1H), 6.77 (d, 1H, J=3.6 Hz), 6.67 (m, 1H); LC-MS: m/z 422 (M+H )+.

Example 9

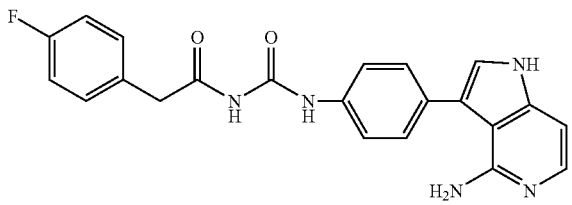

1-(4-(4-Amino-1H-pyrrolo[3,2-c]pyridin-3-yl)phenyl)-3-(2-(4-fluorophenyl)acetyl)urea, hydrochloride salt

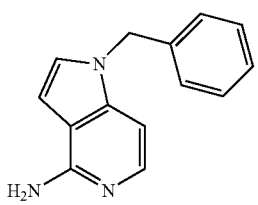

A) 1-Benzyl-1H-pyrrolo[3,2-c]pyridin-4-amine

Benzylamine (1.8 mL, 16.4 mmol, 5 eq) was added to 4-chloro-1H-pyrrolo[2,3-b]pyridine (0.50 g, 3.3 mmol, 1.0 eq; see, generally, Cheng, C.-C. et al. *J. Physical Chem.* 2003, 107, 1459-1471, incorporated by reference in its entirety) in a sealed tube and the reaction mixture was heated at 180° C. for 8 h. The reaction mixture was purified by loading it directly onto a C-18 YMC 30×500 mm reverse phase column (eluting 20-90% aqueous methanol with 0.1% TFA over a 30 minute gradient) and the appropriate fractions were isolated and concentrated in vacuo. The residue was neutralized with saturated aq. NaHCO₃ solution and the mixture was extracted with CHCl₃. The combined organic extracts were dried (Na₂SO₄), filtered and concentrated in vacuo to afford the product (0.40 g, 55%) as a solid. ¹H NMR (DMSO-d₆) δ 7.51-7.52 (m, 1H), 7.16-7.36 (m, 6H), 6.63-6.68 (m, 2H), 6.09 (s, 2H); MS(ESI+) m/z 224 (M+H)+. Calculated: 224.1188, found: 224.1178

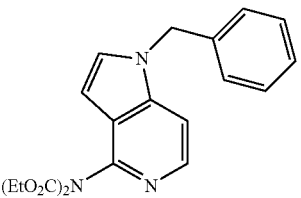

B) Bis-ethyl 1-benzyl-1H-pyrrolo[3,2-c]pyridin-4-yl-dicarbamate

Triethylamine (0.29 mL, 2.1 mmol, 1.2 eq) was added to a solution of 1-benzyl-1H-pyrrolo[3,2-c]pyridin-4-amine (0.39 g, 1.8 mmol, 1.0 eq) and chloroethyl formate (0.18 ml, 1.9 mmol, 1.1 eq) in pyridine (10 mL) at 0° C. The reaction mixture was warmed to room temperature and stirred for 12 h. The reaction mixture was concentrated in vacuo, quenched with saturated aqueous NaCl solution and the resulting mixture was extracted with CHCl₃. The combined organic extracts were dried (Na₂SO₄), filtered and concentrated in vacuo. The residue was purified by silica gel flash chromatography (eluting sequentially with 2/1 hexane/EtOAc then to elute product 0-1% MeOH in CHCl₃) to afford the product (0.23 g, 36%) as a solid. ¹H NMR (CDCl₃) δ 8.13-8.14 (m, 1H), 7.04-7.31 (m, 7H), 6.42-6.43 (m, 1H), 5.26 (s, 2H), 4.17 (q, 4H, J=7.1 Hz), 1.10 (t, 6H, J=7.1 Hz); MS(ESI+) m/z 368 (M+H)+.

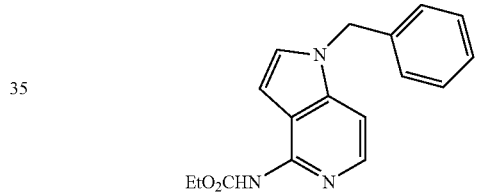

C) Ethyl 1-benzyl-1H-pyrrolo[3,2-c]pyridin-4-ylcarbamate

Sodium hydroxide (1 N, 1.0 mL, 1.0 mmol, 1.7 eq) was added to a solution of bis-ethyl 1-benzyl-1H-pyrrolo[3,2-c]pyridin-4-yl-dicarbamate (0.23 g, 0.63 mmol, 1.0 eq) in EtOH (5 mL) at room temperature and the reaction mixture was stirred for 1 h. The reaction mixture was concentrated in vacuo, diluted with saturated aqueous NaCl solution and extracted with CHCl₃. The combined organic extracts were dried (Na₂SO₄), filtered and concentrated in vacuo to afford the product (0.16 g, 86%) as a solid. ¹H NMR (CDCl₃) δ 7.81 (br s, 1H), 7.19-7.28 (m, 3H), 7.02-7.04 (m, 3H), 6.89-6.90 (m, 2H), 5.23 (s, 2H), 4.20 (q, 2H, J=7.1 Hz), 1.28 (t, 3H, J=7.1 Hz); MS(ESI+) m/z 296 (M+H)+. Calculated: 296.1399, found: 296.1388.

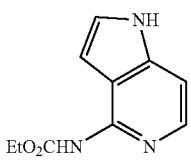

D) Ethyl 1H-pyrrolo[3,2-c]pyridin-4-ylcarbamate

Sodium metal (0.067 g, 2.9 mmol, 10 eq) was added to a solution of ethyl 1-benzyl-1H-pyrrolo[3,2-c]pyridin-4-ylcarbamate (0.086 g, 0.29 mmol, 1.0 eq) in a mixture of liquid NH₃ (5 mL) and THF (1 mL) at −78° C. The dark blue reaction mixture was stirred at −78° C. for 5 minutes and then was quenched with solid NH₄Cl. The clear solution was allowed to warm to room temperature, treated with 10% NaHCO₃ and extracted with 10/1 CHCl₃/MeOH. The combined organic extracts were dried (Na₂SO₄), filtered and concentrated in vacuo to afford the product (0.059 g, 100%) as a solid. ¹H NMR (CD₃OD) δ 7.74 (d, 1H, J=6.0 Hz), 7.21 (d, 1H, J=3.4 Hz), 7.09 (d, 1H, J=5.7Hz), 6.59 (d, 1H, J=3.4Hz), 4.15 (q, 2H, J=7.1 Hz), 1.25 (t, 3H, J=7.1 Hz); MS(ESI⁺) m/z 206 (M+H)⁺. Calculated: 206.0930, found: 206.0932.

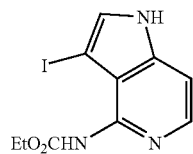

E) Ethyl 3-iodo-1H-pyrrolo[3,2-c]pyridin-4-ylcarbamate

N-Iodosuccinamide (0.030 g, 0.13 mmol, 1.0 eq) was added to a solution of ethyl 1H-pyrrolo[3,2-c]pyridin4-ylcarbamate (0.027 g, 0.13 mmol, 1.0 eq) in THF (1 mL) at room temperature and the reaction mixture was stirred for 15 minutes. The reaction mixture was quenched with 10% NaHSO₃ solution and extracted with 10/1 CHCl₃/MeOH. The combined organic extracts were dried (Na₂SO₄), filtered and concentrated in vacuo. The residue was purified by flash chromatography (SiO₂, eluting 0-5% CHCl₃/MeOH) to afford the product (0.031 g, 72%) as a solid. ¹H NMR (CD₃OD) δ 7.87 (d, 1H, J=5.9 Hz), 7.38 (s, 1H), 7.25 ((d, 1H, J=5.9 Hz), 4.14 (q, 2H, J=7.1 Hz), 1.12 (t, 3H, J=7.1 Hz); MS(ESI⁺) m/z 332 (M+H)⁺. Calculated: 331.9896, found: 331.9884.

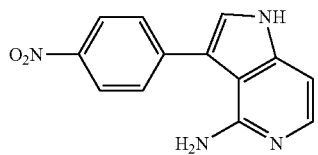

F) 3-(4-Nitrophenyl)-1H-pyrrolo[3,2-c]pyridin-4-amine

Tetrakis(triphenylphosphine)palladium(0) (0.011 g, 0.009 mmol, 0.1 eq) was added to ethyl 3-iodo-1H-pyrrolo[3,2-c]pyridin-4-ylcarbamate (0.031 g, 0.094 mmol, 1.0 eq), sodium carbonate (0.07g, 0.66 mmol, 7.0 eq) and 4-nitrophenyl boronic acid (0.055g, 0.33 mmol, 3.5 eq) in a degassed solution of 1/1 dioxane/water (1 mL) at room temperature. The reaction mixture was heated to 80° C. for 5 h. The reaction mixture was cooled to room temperature and concentrated in vacuo. The residue was dissolved in water and the pH adjusted to 7.0 with dilute aqueous HCl. The solution was extracted with 10/1 CHCl₃/MeOH, the combined organic extracts dried (Na₂SO₄), filtered and concentrated in vacuo. The residue was purified by loading it onto a 1.5 g Varian SCX cationic exchange cartridge (eluting sequentially with 1/1 DCM/MeOH, MeOH, 0.1N NH₃ in MeOH, and to elute the product 1.0 N NH₃ in MeOH) and the appropriate fractions were isolated and concentrated in vacuo to afford the product (0.006 g, 26%) as a solid. MS(ESI⁺) m/z 255 (M+H)⁺. Calculated: 255.0882, found: 255.0887.

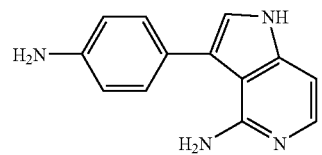

G) 3-(4-Aminophenyl)-1H-pyrrolo[3,2-c]pyridin-4-amine

Platinum oxide (catalytic) was added to a solution of 3-(4-nitrophenyl)-1H-pyrrolo[3,2-c]pyridin4-amine (0.006 g, 0.024 mmol, 1.0 eq) in MeOH (1 mL) and the reaction mixture was stirred at room temperature under a blanket of hydrogen (50 psi) for 1 h. The reaction mixture was filtered through Celite® and the filtrate concentrated in vacuo to afford the product (0.005 g, 100%) as a solid. MS(ESI⁺) m/z 225 (M+H)⁺. Calculated: 225.1140, found: 225.1141.

H) 1-(4-(4-Amino-1H-pyrrolo[3,2-c]pyridin-3-yl)phenyl)-3-(2-(4-fluorophenyl)acetyl)urea, hydrochloride salt 2-(4-Fluorophenyl)acetyl isocyanate (Compound C of Example 3, 0.29 M, 0.062 mL, 0.018 mmol, 2.0 eq) was added to a solution of 3-(4-aminophenyl)-1H-pyrrolo[3,2-c]pyridin-4-amine (0.002 g, 0.009 mmol, 1.0 eq) in 1/1 DCM/CH₃CN (1 mL) and the reaction mixture was stirred at room temperature for 6 h. The reaction mixture was concentrated in vacuo and the residue was purified by flash chromatography (SiO₂, eluting 0-5% MeOH in CHCl₃). The appropriate fractions were isolated and concentrated in vacuo. The residue was dissolved in THF (1 mL), cooled to 0° C. and treated with anhydrous 4 N HCl in dioxane (1 mL, 4.0 mmol, 168 eq). The reaction mixture was stirred at 0° C. for 1 h and the resulting heterogeneous solution was concentrated in vacuo. The residue was triturated with Et₂O, discarding the filtrate and the solid dried in vacuo to afford the title compound (0.002 g, 50%) as a pale yellow solid. MS(ESI⁺) m/z 404 (M+H)⁺.

Example 10

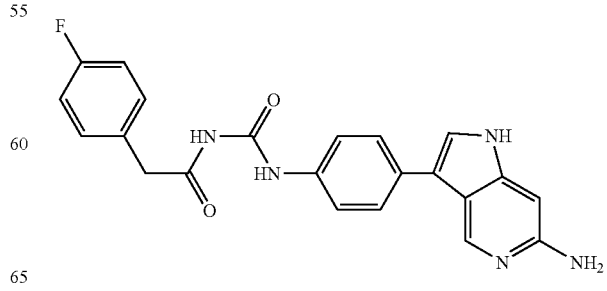

1-(4-(6-Amino-1H-pyrrolo[3,2-c]pyridin-3-yl)phenyl)-3-(2-(4-fluorophenyl)acetyl)urea, trifluoroacetic acid salt

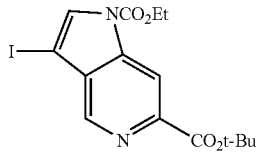

A) 6-tert-Butyl 1-ethyl 3-iodo-1H-pyrrolo[3,2-c]pyridine-1,6-dicarboxylate

To a mixture of tert-butyl 4-(ethoxycarbonyl)-5-(2-(trimethylsilyl)ethynyl) picolinate (Compound D of Example 5, 270 mg, 0.75 mmol) and potassium carbonate (308 mg, 2.25 mmol) in acetonitrile (8 mL) and methanol (2 mL) at 0° C., was added iodine (190 mg, 0.75 mmol). The resulting mixture was stirred at 0° C. for 30 min. The mixture was diluted with EtOAc, washed with brine. The organic layer was dried over MgSO₄ and the desired product was purified by flash column chromatography (silica gel, 20% EtOAc/CH₂Cl₂) to give a light brown solid (232 mg, 74% yield). LC-MS: m/z 417 (M+H)⁺.

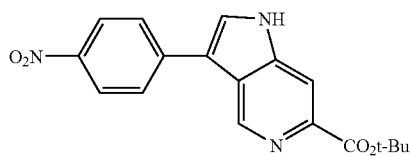

B) tert-Butyl 3-(4-nitrophenyl)-1H-pyrrolo[3,2-c]pyridine-6-carboxylate

To a mixture of 6-tert-butyl 1-ethyl 3-iodo-1H-pyrrolo[3,2-c]pyridine-1,6-dicarboxylate (55 mg, 0.13 mmol) and 4-nitrophenylboronic acid (67 mg, 0.4 mmol) in toluene (3 mL) and ethanol (1.5 mL), was added Pd(PPh₃)₄, followed by K₃PO₄ (2 M, 0.4 mL). The resulting mixture was purged with argon, and heated at 75-80° C. for 5 h. The desired product was purified by prep-HPLC to gave a yellow solid (8 mg, 18 % yield). $^1$H NMR (CDCl₃) δ 8.68 (s, 1H), 8.30 (d, 2H, J=8.8 Hz), 8.00 (d, 1H, J=8.8 Hz), 7.36 (s, 1H), 7.25 (s, 1H), 1.51 (s,9H) ; LC-MS: m/z 284 (M-Bu)⁺.

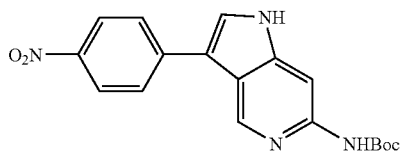

C) tert-Butyl 3-(4-nitrophenyl)-1H-pyrrolo[3,2-c]pyridin-6-ylcarbamate

The titled compound was obtained as a yellow solid (48% yield) from tert-butyl 3-(4-nitrophenyl)-1H-pyrrolo[3,2-c]pyridine-6-carboxylate by a similar procedure to that of Step G of Example 5 with the exception of using dimethylacetamide (¼ volume) as co-solvent. LC-MS: m/z 355 (M+H)⁺.

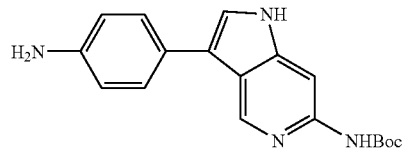

D) tert-Butyl 3-(4-aminophenyl)-1H-pyrrolo[3,2-c]pyridin-6-ylcarbamate

The title compound was obtained as an off white solid (quantitative yield) from tert-butyl 3-(4-nitrophenyl)-1H-pyrrolo[3,2-c]pyridin-6-ylcarbamate by a similar procedure to that of Step H of Example 5. LC-MS: m/z 325 (M+H)⁺.

E) 1-(4-(6-Amino-1H-pyrrolo[3,2-c]pyridin-3-yl)phenyl)-3-(2-(4-fluorophenyl)acetyl)urea The title compound was obtained as a white solid (17% yield) and as a TFA salt from tert-butyl 3-(4-aminophenyl)-1H-pyrrolo[3,2-c]pyridin-6-ylcarbamate by a similar procedure to that of Step I of Example 5. $^1$H NMR (CD₃OD) δ 8.13 (s, 1H), 7.66 (d, 2H, J=8.4 Hz), 7.55 (d, 2H, J=8.8 Hz), 7.27 (m, 2H), 7.00 (m, 2H), 6.80 (s, 1H), 6.68 (s, 1H), 3.62 (s, 2H); LC-MS: m/z 404 (M+H)⁺.

We claim:

1. A compound having formula I:

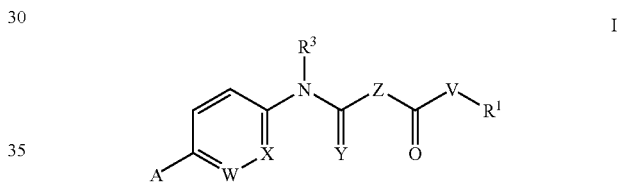

or an enantiomer, diastereomer, pharmaceutically acceptable salt, thereof, wherein:

$R^1$ is selected from the group consisting of H, alkyl, substituted alkyl, alkenyl, substituted alkenyl, alkynyl, substituted alkynyl, cycloalkyl, substituted cycloalkyl, aryl, and substituted aryl;

V is $CH_2$ or $NR^8$;

W and X are each CH;

Y is O, S, or $NR^9$;

Z is —$CR^{10}R^{11}$— or —$(CR^{10}R^{11})_m NR^{12}$—;

m is 0 to 2;

A is:

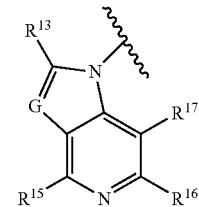

wherein

G is $CR^{14}$ or N;

$R^3$, $R^8$ and $R^{12}$ are independently H, alkyl, substituted alkyl, alkenyl, substituted alkenyl, alkynyl, substituted alkynyl, cycloalkyl, substituted cycloalkyl, aryl, and/or substituted aryl;

$R^9$ is H, alkyl, substituted alkyl, CN, $NO_2$ or $SO_2$Amino;

$R^{10}$ and $R^{11}$ are independently H, halogen, alkyl, substituted alkyl, cycloalkyl, substituted cycloalkyl, aryl, and/or substituted aryl, or taken together to form a carbocyclic ring having from 3 to 8 atoms;

$R^{13}$, $R^{15}$, $R^{16}$, $R^{17}$, are independently H, halogen, $NR^{27}R^{28}$, $OR^{29}$, $CO_2R^{30}$, $CO_2NR^{31}R^{32}$, $SO_2R^{33}$, alkyl, substituted alkyl, alkenyl, substituted alkenyl, cycloalkyl, substituted cycloalkyl, aryl, and/or substituted aryl;

$R^{14}$ is H, halogen, $NR^{27}R^{28}$, $COR^{30}$, $CONR^{31}R^{32}$, $SO_2R^{33}$, alkyl, substituted alkyl, cycloalkyl, substituted cycloalkyl, aryl, and/or substituted aryl; and $R^{27}$, $R^{28}$, $R^{29}$, $R^{30}$, $R^{31}$, $R^{32}$ and $R^{33}$ are each independently H, alkyl, substituted alkyl, cycloalkyl, substituted cycloalkyl, aryl, and/or substituted aryl;

wherein:

each of said substituted alkyl, each of said substituted alkenyl, and each of said substituted alkynyl are substituted with one or more substituents independently selected from the group consisting of alkyl, cycloalkyl, aryl, halogen, haloalkyl, alkoxy, alkylthio, hydroxy, —COOH, alkyloxycarbonyl, alkylcarbonyloxy, —$NH_2$, and thiol;

each of said substituted cycloalkyl is substituted with one or more substituents independently selected from the group consisting of halogen, hydroxyl, alkyl, alkoxy, —$NH_2$, nitro, cyano, thiol, and alkylthio; and each of said substituted aryl is substituted with one or more substituents independently selected from the group consisting of halogen, alkyl, alkoxy, hydroxy, —COOH, alkyloxycarbonyl, nitro, trifluoromethyl, —$NH_2$, cyano, and thiol.

2. The compound according to claim 1 wherein Y is O or S.

3. The compound according to claim 1 wherein A is:

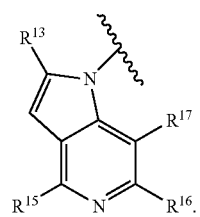

4. The compound according to claim 1 wherein $R^3$ is $R^3$ is H.

5. The compound according to claim 1 wherein V is NH and Z is $CH_2$.

6. The compound according to claim 1 wherein V is $CH_2$ and Z is NH.

7. The compound according to claim 1 wherein $R^1$ is phenyl, $C_1$ to $C_5$ alkyl, or $C_3$ to $C_7$ cycloalkyl.

8. The compound according to claim 1 wherein $R^1$ is a halo substituted phenyl.

9. The compound according to claim 1 wherein $R^1$ is fluorophenyl.

10. The compound according to claim 1 wherein $R^1$ is phenyl, $R^3$ is H, Y is O or S, Z is NH or $CH_2$.

11. A compound according to claim 1 selected from the group consisting of:

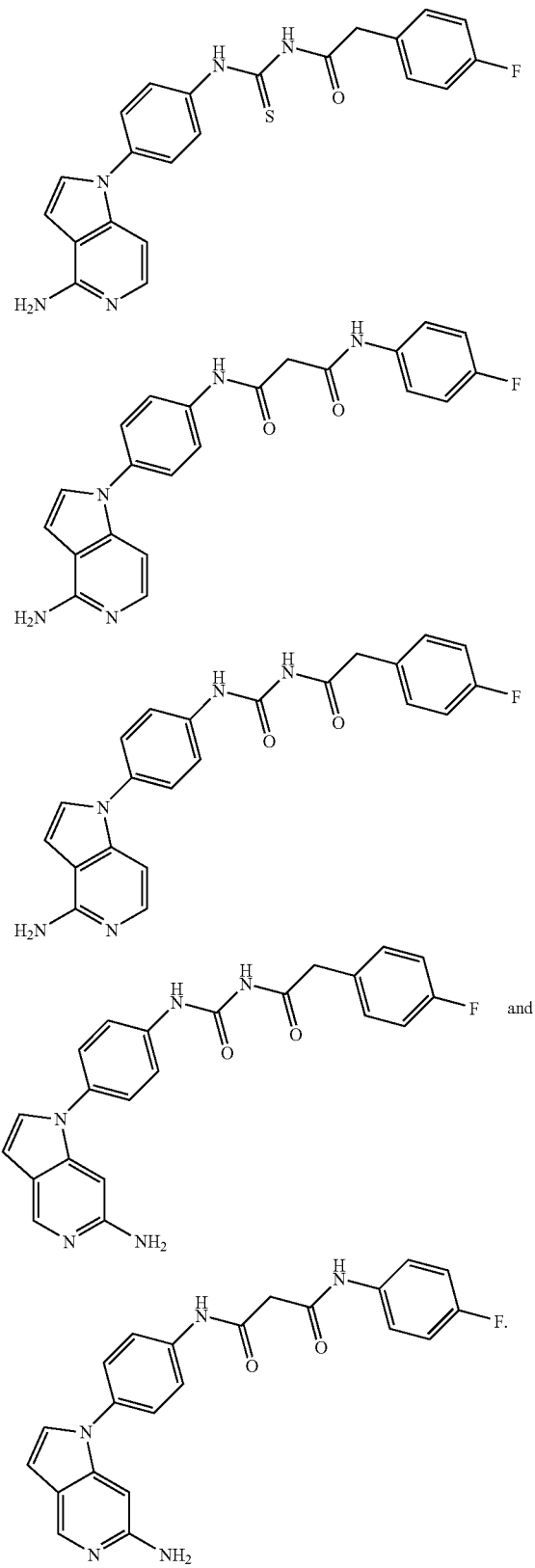

* * * * *

UNITED STATES PATENT AND TRADEMARK OFFICE
CERTIFICATE OF CORRECTION

PATENT NO. : 7,566,784 B2  
APPLICATION NO. : 11/113838  
DATED : July 28, 2009  
INVENTOR(S) : Borzilleri et al.

Page 1 of 1

It is certified that error appears in the above-identified patent and that said Letters Patent is hereby corrected as shown below:

In Column 42:

Line 38, In Claim 1, delete "diastereomer," and insert -- diastereomer, or --

Line 63, In Claim 1, delete "CR14 or N;" and insert -- $CR^{14}$; --

In Column 43:

Line 6, In Claim 1, delete "$R^{16}$, $R^{17}$," and insert -- $R^{16}$, and $R^{17}$ --

Line 49, In Claim 4, after "$R^3$ is" delete "$R^3$ is"

Line 64, In Claim 10, delete "S, Z" and insert -- S, and Z --

Signed and Sealed this

Twentieth Day of April, 2010

David J. Kappos
*Director of the United States Patent and Trademark Office*